(12) United States Patent
Sidorov et al.

(10) Patent No.: US 9,267,144 B2
(45) Date of Patent: Feb. 23, 2016

(54) PLASTID TRANSFORMATION OF MAIZE

(75) Inventors: Vladimir Sidorov, Chesterfield, MO (US); Jeffrey M. Staub, Wildwood, MO (US); Yuechun Wan, Madison, WI (US); Guangning Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1151 days.

(21) Appl. No.: 12/106,073

(22) Filed: Apr. 18, 2008

(65) Prior Publication Data
US 2008/0289063 A1 Nov. 20, 2008

Related U.S. Application Data

(60) Continuation of application No. 11/244,263, filed on Oct. 5, 2005, now abandoned, which is a division of application No. 10/248,492, filed on Jan. 23, 2003, now abandoned.

(60) Provisional application No. 60/319,095, filed on Jan. 23, 2002.

(51) Int. Cl.
*C12N 15/82* (2006.01)

(52) U.S. Cl.
CPC .................................. *C12N 15/8214* (2013.01)

(58) Field of Classification Search
None
See application file for complete search history.

(56) References Cited

U.S. PATENT DOCUMENTS

| | | | | |
|---|---|---|---|---|
| 5,627,061 A * | 5/1997 | Barry et al. | ................. | 800/288 |
| 5,693,507 A | 12/1997 | Daniell et al. | | |
| 5,767,368 A | 6/1998 | Zhong et al. | | |
| 6,603,061 B1 * | 8/2003 | Armstrong et al. | ........... | 800/294 |
| 7,129,391 B1 * | 10/2006 | Daniell | ........................ | 800/278 |
| 7,803,991 B2 * | 9/2010 | Daniell | ........................ | 800/300 |
| 2002/0042934 A1 * | 4/2002 | Staub et al. | ................... | 800/300 |
| 2005/0198704 A1 | 9/2005 | Sticklen | | |

FOREIGN PATENT DOCUMENTS

WO   WO 99/10513   *   3/1999

OTHER PUBLICATIONS

Zhong et al (1996, Plant Physiol. 110:1097-1107).*
Khan and Maliga, "Fluorescent antibiotic resistance marker for tracking plastid transformation in higher plants." Nat Biotechnol. Sep. 1999;17(9):910-5.
Maier et al., "Complete sequence of the maize chloroplast genome: gene content, hotspots of divergence and fine tuning of genetic information by transcript editing." J Mol Biol. Sep. 1, 1995;251(5):614-28.
Sidorov et al., "Technical Advance: Stable chloroplast transformation in potato: use of green fluorescent protein as a plastid marker." Plant J. Jul. 1999;19(2):209-216.
Sikdar et al., "Plastid transformation in Arabidopsis thaliana." vol. 18, Nos. 1-2 / Nov. 1998 Plant Cell Reports 1 8:20-24, 1998;.
Staub and Maliga, "Long regions of homologous DNA are incorporated into the tobacco plastid genome by transformation." Plant Cell. Jan. 1992;4(1):39-45.
Staub et al., "High-yield production of a human therapeutic protein in tobacco chloroplasts." Nat Biotechnol. Mar. 2000;18(3):333-8.
Svab and Maliga, "High-frequency plastid transformation in tobacco by selection for a chimeric aadA gene." Proc Natl Acad Sci U S A. Feb. 1, 1993;90(3):913-7.
Svab et al., "Stable transformation of plastids in higher plants." Proc Natl Acad Sci U S A. Nov. 1990;87(21):8526-30.
Zhong et al., "The Competence of Maize Shoot Meristems for Integrative Transformation and Inherited Expression of Transgenes." Plant Physiol. Apr. 1996;110(4):1097-1107.
Zoubenko et al., "Efficient targeting of foreign genes into the tobacco plastid genome." Nucleic Acids Res. Sep. 25, 1994;22(19):3819-24.
Ahmadabadi, Mohammad et al., A leaf-based regeneration and transformation system for maize (*Zea mays* L.), Transgenic Res (2007) 16:437-448.
Bogorad, Lawrence, Engineering chloroplasts: an alternative site for foreign genes, proteins, reactions and products, Tibtech Jun. 2000, vol. 18, pp. 257-263.
Daniell, Henry et al., Breakthrough in chloroplast genetic engineering of agronomically important crops, Trends in Biotechnology, vol. 23, No. 5, May 2005, pp. 238-245.
Lee, Sa Mi et al., Plastid Transformation in the Monocotyledonous Cereal Crop, Rice (*Oryza sativa*) and Transmission of Transgenes to Their Progeny, Mol. Cells, vol. 21, No. 3, pp. 401-410 (2006).
Verma, Dheeraj et al., Chloroplast Vector Systems for Biotechnology Applications, Plant Physiology, Dec. 2007, vol. 145, pp. 1129-1143.
Clarke, Jihong Liu et al., Chloroplast Biotechnology, Genomics and Evolution: Current Status, Challenges and Future Directions, Plant Molecular Biology, May 18, 2011, pp. 207-209, vol. 76.
Dhingra, Amit et al., Chloroplast Genetic Engineering Via Organogenesis or Somatic Embryogenesis, Methods in Molecular Biology, 2006, pp. 245-262, vol. 323.
Daniell, Henry et al., Expression of the Native Cholera Toxin B Subunit Gene and Assembly as Functional Oligomers in Transgenic Tobacco Chloroplasts, Journal of Molecular Biology, 2001, pp. 1001-1009, vol. 311.
Svab, Zora et al., High-Frequency Plastid Transformation in Tobacco by Selection for a Chimeric aadA Gene, Proceedings of the National Academy of Sciences, Feb. 1993, pp. 913-917, vol. 90.

* cited by examiner

*Primary Examiner* — Anne Kubelik
(74) *Attorney, Agent, or Firm* — Thompson Coburn LLP; J. Wendy Davis

(57) ABSTRACT

A method is provided for transforming maize plants to express DNA sequences of interest from plant cell plastids. The method allows the transformation of maize plant tissue with heterologous DNA constructs by microprojectile bombardment of green light grown cultures and dark grown embryogenic cultures. The invention also provides for maize cells in which the plastids contain heterologous DNA constructs.

14 Claims, 14 Drawing Sheets

```
                              SEQUENCE LISTING

<160> NUMBER OF SEQ ID NOS: 35

<210> SEQ ID NO 1
<211> LENGTH: 22
<212> TYPE: DNA
<213> ORGANISM: Artificial
<220> FEATURE:
<223> OTHER INFORMATION: synthetic construct

<400> SEQUENCE: 1
tgaaatagat cttgatacga tc                                                  22

<210> SEQ ID NO 2
<211> LENGTH: 27
<212> TYPE: DNA
<213> ORGANISM: Artificial
<220> FEATURE:
<223> OTHER INFORMATION: synthetic construct

<400> SEQUENCE: 2
gcggccgctc aaaagaaagc tattgtg                                             27

<210> SEQ ID NO 3
<211> LENGTH: 38
<212> TYPE: DNA
<213> ORGANISM: Artificial
<220> FEATURE:
<223> OTHER INFORMATION: synthetic construct

<400> SEQUENCE: 3
agctttcttt tgagcggccg catccaattt caagttcg                                 38

<210> SEQ ID NO 4
<211> LENGTH: 25
<212> TYPE: DNA
<213> ORGANISM: Artificial
<220> FEATURE:
<223> OTHER INFORMATION: synthetic construct

<400> SEQUENCE: 4
agtggatcca cttaaaaaaa aaaac                                               25

<210> SEQ ID NO 5
<211> LENGTH: 27
<212> TYPE: DNA
<213> ORGANISM: Artificial
<220> FEATURE:
<223> OTHER INFORMATION: synthetic construct

<400> SEQUENCE: 5
ggctcgagct gcggaatctt ctactgg                                             27

<210> SEQ ID NO 6
<211> LENGTH: 23
<212> TYPE: DNA
<213> ORGANISM: Artificial
<220> FEATURE:
<223> OTHER INFORMATION: synthetic construct

<400> SEQUENCE: 6
```
cgcatgtacc tgcagtcgca ttc                                                23

<210> SEQ ID NO 7
<211> LENGTH: 3438
<212> TYPE: DNA
<213> ORGANISM: Zea mays

<400> SEQUENCE: 7

```
ggtaccgggc cccccctcga gctgcggaat cttctactgg tacatggaca actgtttgga      60
ctgatggact taccagtctt gatcgttaca aaggacgatg ctatcacatc gagcccgttc     120
ctggggaccc agatcaatat atctgttatg tagcttatcc attagaccta tttgaagagg     180
gttctgttac taacatgttt acttccattg tgggtaacgt atttggtttc aaagccttac     240
gcgctctacg tttggaggat ctacgaattc cccctgctta ttcaaaaact ttccaaggtc     300
cgcctcacgg tatccaagtt gaaagggata agttgaacaa gtacggtcgt cctttattgg     360
gatgtactat taaaccaaaa ttgggattat ccgcaaaaaa ttacggtaga gcgtgttatg     420
agtgtctacg cggtggactt gattttacca aagatgatga aaacgtaaac tcacaaccat     480
ttatgcgctg gagagaccgt ttcgtctttt gtgccgaagc aatttataaa gcacaagccg     540
aaactggtga aatcaagggg cattacttga atgcgactgc aggtacatgc gaagaaatga     600
ttaagagagc tgtatttgca agggaattag gggttcctat tgtaatgcat gactacttaa     660
caggaggatt caccgcaaat actactttgt ctcattattg ccgcgacaac ggcctacttc     720
ttcacattca ccgagcaatg catgcagtta ttgatagaca gaaaaatcat ggtatgcatt     780
tccgtgtatt agctaaagca ttgcgtatgt cggggggaga tcatatccac tccggtacag     840
tagtaggtaa gttagaaggg gaacgcgaaa taactttagg ttttgttgat ttattgcgcg     900
atgattttat tgaaaaagat cgttctcgcg gtatcttttt cactcaggac tgggtatcca     960
tgccaggtgt tataccggtg gcttctgggg gtattcatgt ttggcatatg ccagctctga    1020
ccgaaatctt tggagatgat tccgtattac aatttggtgg aggaactttta ggacatcctt    1080
ggggaaatgc acctggtgca gcagctaatc gtgtggcttt agaagcctgt gtacaagctc    1140
gtaacgaagg gcgcgatctt gctcgtgaag gtaatgaaat tatcaaagca gcttgcaaat    1200
ggagtgctga actagccgca gcttgtgaaa tatggaagga gatcaaattt gatggtttca    1260
aagcgatgga taccatataa aataaaaaaa aaagcaaaat agaagagaaa aaataagtt     1320
aagaaatgca gtaattcttc tttattcttc taattgattg caattcaatt cggctcaatc    1380
ttttctaaaa aaaaaaaaga ctgagccgaa ttgaaataga tcttgatacg atcatgagac    1440
ttgacaaatc gagattcttc tattctatat atctagaata tagaaaggta taatacaata    1500
aacaaatata aatcaaaata tagtattatc gtacgataat ggaatcaaat acgcagtatt    1560
tacagaaaag agtcttcgtt tattgggaaa gaatcaatat acttttaatg tcgaatcggg    1620
attcactaag acagaaataa agcattgggt cgaactcttc tttggtgtta aggtagtagc    1680
tgtgaatagc catcgactac ccggaaaggt agaagaatgg gacctattct gggacataca    1740
atgcattaca gacgtatgat cattacccctt caactgggta ttctattcca cttctacttt    1800
ttaaattaaa gggtattctg aaagaggtat ttcttttatt ttcacaatag ctttcttttg    1860
agcggccgca tccaatttca agttcgatta gaaggataga aaggcgatga gaatgggaaa    1920
agaaaaataa aatattttat tttaatgagt tccccttttg agttcccctt ttttgcaatt    1980
ttcttattat caattccatt catttatttt atagaatact ttttattct atatctataa    2040
aaaatcttta ttttgtaaac taaaaaatac aatagtcaat attccttata atagatatac    2100
```

```
ttaattatat cataagaatc ttaagatata tttcgaatag atagaaatag taaatttgaa      2160
ttgagacaca tattctatga cagattttaa cttaccctct attttcgtac ctttagtagg      2220
cttagtattt ccggcaattg caatgacttc cttatttctt tatgtgcaga aaaataagat      2280
tgtctagaaa cgacgggcc aaattttctc aatgtatttc caggatcata atacagatat      2340
ttttttgtgt aagtactata atatgatagg gtatgtagct cttctacac acaaatgaaa      2400 aacgtctatg gatgcagata taagctacga gcataaatgc atgcatatgc gtagccgact      2460
atagcgagtt ttttttttta agtggatcca ctaattttt ttgaatagaa agtcaatgta      2520
tctaaccaat tatttcacag gagtactagc tactgaaggc tatttcagaa tcaaaaaaag      2580
taaagtgaaa aatcatttag cttattctct caatttcaat tgaccgctac tggatttagt      2640
atatctaata tgaattggcg atcagaacac atatggatag aacttctaaa aggttctcga      2700
aaaagaggta atttttttctg ggcctgtatt cttttttctag gttcattagg attcttagcg      2760
gttgggcctt ccagttatct tggtaagaat atgatatctg tacttccatc tcaacaaatt      2820
cttttttttc cacaggggt cgtgatgtct ttctacggaa tcgcgggcct attcattagc      2880
tcctatttgt ggtgcactat tttatggaat gtaggcagtg ttatgaccg attcgataga      2940 aaagagggaa tagtgtgcat ttttcgttgg ggattccctg gaataaaacg tcgcatcttc      3000
cttcaattcc ttgtgcggga tatccaatca attagaattc aggttaaaga gggtctttat      3060
cctcgtcgta tccttatat ggaaatccgg ggccaggggg tcattcccctt gactcgtact      3120 gatgagaagt tttttactcc acgagaaatt gaacaaaaag ctgccgaatt ggcctatttc      3180
ttgcgtgtac caattgaagt attttgagta ccaattgcaa ttttttgcaa ttgtaagggg      3240 atttttcgagt atttatctaa agtaaaggaa ggaacaaacg aggataagag aaaattgctt      3300
cgaatttgtt ttgtccaagt gagatatatg gcatactatt cttccattt tatacgaaag      3360 gccttttttt atttctctat tccactccat ttagatctaa gaaagaaccc aatacaatga      3420
aattccacta gttctaga                                                    3438

<210> SEQ ID NO 8
<211> LENGTH: 4852
<212> TYPE: DNA
<213> ORGANISM: Zea mays

<400> SEQUENCE: 8
ggtaccgtcg acttatcagg ggcgcgctct accactgagc taatagcccg tcgcgcggcc        60
tcccaaaggg aggccgctac gccaaaagcg agaaaaactc catcccttc ctttttgacat       120 ccccatgccg ccacacgggg ggacatgggg acgtcaaaaa ggggatccta tcactatcaa       180
ctaatttgtt ccgacctagg ataataagct catgagcttg gtcttacttc accctaaacg       240
aaagaagact tccatatcca agtttagctc agacgtagct gccttctttt tgggcgtgaa       300
gcagtgtcaa accaaaatac ccaataagca taagcattag ctctccctga aaaggaggtg       360
atccagccgc accttccagt acggctacct tgttacgact tcactccagt cgcaagccta       420
gccttaggca tccccctcct tacggttaag ggtaatgact tcaaacctgg ccagctccta       480
tagtgtgacg ggcggtgtgt acaaggcccg ggaacggatt cgccgccgta tggctgaccg       540
gcgattacta gcgattcctg cttcatgcag gcgagttgca gcctgcaatc cgaactgagg       600
acgggttttt ggagttagct caccctcgcg agatcgcgac cctttgtccc gcccattgta       660
gcacgtgtgt cgcccagggc ataaggggca tgatgacttg gcctcatcct ctccttcctc       720
```

```
cggcttaaca ccggcggtct gttcagggtt ccaaactcat agtggcaact aaacacgagg    780
gttgcgctcg ttgcgagact taacccaaca ccttacggca cgagctgacg acagccatgc    840
accacctgtg tccgcgttcc cgagggcacc cctctctttc aagaggattc gcggcatgtc    900
aagccctggt aaggttcttc gccttgcatc gaattaaacc acatgctcca ccgcttgtgc    960
gggcccccgt caattccttt gagtttcatt cttgcgaacg tactcccag gcgggatact     1020
taacgcgtta gctacagcac tgcacgggtc gagtcgcaca gcacctagta tccatcgttt    1080
acggctagga ctactggggt ctctaatccc atttgctccc ctagctttcg tctctcagtg    1140
tcagtgtcgg cccagcagag tgctttcgcc gttggtgttc tttccgatct caatgcattt    1200
caccgctcca ccggaaattc cctctgcccc taccgtactc cagcttggta gtttccaccg    1260
cctgtccagg gttgagccct gggatttgac ggcggacttg aaaagccacc tacagacgct    1320
ttacgcccaa tcattccgga taacgcttgc atcctctgtc ttaccgcggc tgctggcaca    1380
gagttagccg atgcttattc ctcagatacc gtcattgttt cttctccgag aaaagaagtt    1440
gacgacccgt aggccttcca cctccacgcg gcattgctcc gtcaggcttt cgcccattgc    1500
ggaaaattcc ccactgctgc ctcccgtagg agtctgggcc gtgtctcagt cccagtgtgg    1560
ctgatcatcc tctcggacca gctactgatc atcgccttgg taagctattg cctcaccaac    1620
tagctaatca gacgcgagcc cctccttggg cggatttctc cttttgctcc tcagcctacg    1680
gggtattagc aaccgtttcc agttgttgtt cccctcccaa gggcaggttc ttacgcgtta    1740
ctcacccgtt cgccactgga aacaccactt cccgttcgac ttgcatgtgt taagcatgcc    1800
gccagcgttc atcctgagcc aggatcgaac tctccatgag attcatagtt gcattactta    1860
tagcttcctt attcgtagac aaagcggatt cggaattgtc tttccttcca aggataactt    1920
gtatccatgc gcttcagatt attagcctgg agttcgccac cagcagtata gccaacccta    1980
ccctatcacg tcaatcccac aagcctccta tccattcccg ttcgatcgtg gtggggagt    2040
aagtcaaaat agaaaaaact cacattaggt ttagggataa tcaggctcga actgatgact    2100
tccaccacgt caaggtgaca ctctaccgct gagttatatc ccttcccgt cccatcgaga     2160
aagagaatta acgaatccta aggcaaaggg gcgagaaacg caaggccact cttcctccgg    2220
gctttctttc cgcactatta tggacagtca ataatggga aaaattggat tcaattgtca     2280
acccggcggc cgctcctatc gaaaatagga ttgactatgg attcgagcca tagcacatgg    2340
tttcataaaa tctgtacgat tttcccgatc taaatcgagt gggtttccat gaagaagatc    2400
ttgttcagca tgttctattc gatactggta ggagaagaac ccgactcggt attcttaaaa    2460
aaagagggga agcagaacca agtcaagatg atatggatcg ccccttcttc ttgcgccaaa    2520
gatcttacca tttccgaagg aactgggct acatttcctt tccatttcca ttccagagtt     2580
tctatctgtt tccacgccct tttttgaga cctcgaaaca tgaaatggac aaattccttc     2640
tcttaggaac acatcaaga aaaggataa tggtagcccc cccattaact aatttatgaa      2700
tttcatagta atagaaatcc atgtcctacc gagacagaat ttcgaacttg ctatcctctt    2760
gcctaatagg caaagattga cctctgtaga aagactgatt cattcggatc gatatgagga    2820
cccaactccg ttgcattgcc agaatccatg ttccatattt gaagcgggtt gacctctgtg    2880
cttctctcat ggtacaatcc tcttcctgct gagccccctt tctcctcggt ccacagagaa    2940
aaaatgtagg actggtgccg acagttcatc acggaagaaa gaactcacag agccggggat    3000
cgctaactaa tagaatagta ctactaacta atactaaatat atagataact aatactaata    3060
tatagatatt aatactaata tatagatata tagaaataga tatctagaaa tagaaacgaa    3120
```

```
ctaatatata gataatcgaa atcgaaaaga actgtctttt ctgtatactt tccccgttct    3180
atgctaccgc gggtcttatg caatcgatcg gatcatatag atatcccttc aacacaacat    3240
aggtcatcga aaggatctcg gacgactcac caaagcacga aagccagtta gaaaatggat    3300
tcctatttga agagtgccta accgcatgga taagctcaca ttaacccgtc aattttggat    3360
ccaattcggg atttttcttg ggaagtttcg ggaagaaatt ggataatat cgattcatac    3420
agaggaaaaa gttctctatt gatgcaaacg ctgtacctca gaggataggg atagaggaag    3480
agggaaaaat cgaaatgaaa taaataaaga ataaagccaa aaaataagt cgaagataga    3540
agagcccaga ttcaaaatga agaaatggaa actcgaaaag gatccttctg attctcaaag    3600
aatgaggggc aaggggattg ataccgagaa agatttcttc ttattataag acgtgatttg    3660
atccgcatat gtttggtaaa agaacaatct tctcctttaa tcataaatgg aaagtgttca    3720
attagaacat gaaaacgtga ctcaattggt cttagttagt cttcgggacg gagtggaaga    3780
agggcggaga ctctcgaacg aggaaaagga tcccttcgaa agaattgaac gaggagccgt    3840
atgaggtgaa aatctcatgt acggttctgt agagggacag taaggatgac ttatctgtcg    3900
acttttccac tatcaacccc aaaaaaccca actctgcctt acgtaaagtt gccagagtac    3960
gattaacctc tggatttgaa atcactgctt atatacctgg tattggccat aatttacaag    4020
aacattctgt agtattagta agaggaggaa gggttaagga tttacccggt gtgagatatc    4080
gcattattcg aggaacccta gatgctgtcg cagtaaagaa tcgtcaacaa gggcgttcta    4140
gtgcgttgta gattcttatc caagacttgt atcatttgat gatgccatgt gaatcgctag    4200
aaacatgtga agtgtatggc taacccaata acgaaagttt cgtaagggga ctggagcagg    4260
ctaccatgag acaaaagatc ttctttctaa agagattcga ttcggaactc ttatatgtcc    4320
aaggtcaata tggaaattct ttcagaggtt ttcccttact ttgtccgtgt caacaaacaa    4380
ttcgaaatac ctcgactttt tcagaacagg tccgagtcaa atagcaatga ttcgaagcac    4440
ttcttttttcc attacactat ttcggaaacc taaggactcg atcgtatgga tatggaaaat    4500
acaggatttc cggtcctagc gggaaaagga gggaacgga tactcaattt aaagtgagta    4560
aacagaattc catactcgat ctcatagatc cctatagaat tctgtggaaa gccgtattcg    4620
atgaaagtcg tatgtacggc ttggagggag atctttccta tctttcgaga tccaccctac    4680
aatatgggc caaaaagcca aaaaataag tgattcgttt ttagccctta taaaagaaa    4740
acggattctt gaacctcttt cacgctcatg tcacgtcgag gtactgcaga aaaaagaacc    4800
gcaaaatccg atccaatttt tcgtaatcga ttagttaaca tggtggcccg gg         4852
```

<210> SEQ ID NO 9
<211> LENGTH: 50
<212> TYPE: DNA
<213> ORGANISM: Artificial
<220> FEATURE:
<223> OTHER INFORMATION: synthetic construct

<400> SEQUENCE: 9

```
gggtaccgtc gacttatcag gggcgcgctc taccactgag ctaatagccc              50
```

<210> SEQ ID NO 10
<211> LENGTH: 54
<212> TYPE: DNA
<213> ORGANISM: Artificial
<220> FEATURE:
<223> OTHER INFORMATION: synthetic construct

```
<400> SEQUENCE: 10
taagcttgcg gccgcccggt tgacaattga atccaattt tcccattatt tgac          54

<210> SEQ ID NO 11
<211> LENGTH: 52
<212> TYPE: DNA
<213> ORGANISM: Artificial
<220> FEATURE:
<223> OTHER INFORMATION: synthetic construct

<400> SEQUENCE: 11
aactagtccc gggccaccat gttaactaat cgattacgaa aaattggatc gg            52

<210> SEQ ID NO 12
<211> LENGTH: 51
<212> TYPE: DNA
<213> ORGANISM: Artificial
<220> FEATURE:
<223> OTHER INFORMATION: synthetic construct

<400> SEQUENCE: 12
ggaattcgcg gccgctccta tcgaaaatag gattgactat ggattcgagc c             51

<210> SEQ ID NO 13
<211> LENGTH: 156
<212> TYPE: DNA
<213> ORGANISM: Zea mays

<400> SEQUENCE: 13
ggaattcact cccccaccac gatcgaacgg gaatggatag gaggcttgtg ggattgacgt    60
gatagggtag ggttggctat actgctggtg gcgaactcca ggctaataat ctgaagcgct   120
tggatacaag ttatccttgg aaggaaagac aattcc                             156

<210> SEQ ID NO 14
<211> LENGTH: 211
<212> TYPE: DNA
<213> ORGANISM: Zea mays
<220> FEATURE:
<221> NAME/KEY: promoter
<222> LOCATION: (1)..(160)
<220> FEATURE:
<221> NAME/KEY: misc_feature
<222> LOCATION: (161)..(208)
<223> OTHER INFORMATION: G10L sequence

<400> SEQUENCE: 14
gcggccaatt cactccccca ccacgatcga acgggaatgg ataggaggct tgtgggattg    60
acgtgatagg gtagggttgg ctatactgct ggtggcgaac tccaggctaa taatctgaag   120
cgcatggata caagttatcc ttggaaggaa agacaattcc ggatcctgta gaaataattt   180
tgtttaactt taagaaggag atatacccat g                                  211

<210> SEQ ID NO 15
<211> LENGTH: 162
<212> TYPE: DNA
<213> ORGANISM: Nicotiana tabacum

<400> SEQUENCE: 15
gggtgcagaa attcaattaa ggaaataaat taaggaaata caaaaagggg ggtagtcatt    60
tgtatataac tttgtatgac ttttctcttc tatttttttg tatttcctcc ctttcctttt   120
ctatttgtat ttttttatca ttgcttccat tgaattaagc tt                      162
```

<210> SEQ ID NO 16
<211> LENGTH: 236
<212> TYPE: DNA
<213> ORGANISM: Nicotiana tabacum
<220> FEATURE:
<221> NAME/KEY: promoter
<222> LOCATION: (1)..(95)
<220> FEATURE:
<221> NAME/KEY: misc_feature
<222> LOCATION: (96)..(185)
<223> OTHER INFORMATION: plastid atpB gene leader
<220> FEATURE:
<221> NAME/KEY: misc_feature
<222> LOCATION: (186)..(236)
<223> OTHER INFORMATION: plastid atpB gene (first 15 aa)

<400> SEQUENCE: 16
aagcttgatc tcgctccccc gccgtcgttc aatgagaatg gataagaggc tcgtgggatt    60
gacgtgaggg ggcagggatg gctatatttc tgggagaatt aaccgatcga cgtgcaagcg   120 gacattatt ttaaattcga taattttgc aaaaacattt cgacatattt atttatttta    180
ttattatgag aatcaatcct actacttctg gttctggggt ttccacggct agcatg        236

<210> SEQ ID NO 17
<211> LENGTH: 158
<212> TYPE: DNA
<213> ORGANISM: Zea mays

<400> SEQUENCE: 17
tctagattta gggatttttc gagttgattc attccaccgc gaagtcccct gcatgggtat    60
ctaggaaata gttacttcca agtgaatctt ccctagatac ctaaaatcta ttttattatg   120
atccatttcg cgaaaatata gattaagcta gcggccgc                           158

<210> SEQ ID NO 18
<211> LENGTH: 223
<212> TYPE: DNA
<213> ORGANISM: Zea mays

<400> SEQUENCE: 18
ggctctagaa ataaaaaaaa aagcaaaata gaaagagaaa aaataagtta agaaatgcag    60
taattcttct ttattcctct aattgattgc aattcaattc ggctcaatct tttctaaaaa   120
aaaaaaagac tgagccgaat tgaaatagat cttgatacga tcatgagact tgacaaatcg   180
agattcttct attctatata tcaagaatat agaaaggtaa gct                     223

<210> SEQ ID NO 19
<211> LENGTH: 249
<212> TYPE: DNA
<213> ORGANISM: Zea mays
<220> FEATURE:
<221> NAME/KEY: promoter
<222> LOCATION: (1)..(156)
<220> FEATURE:
<221> NAME/KEY: misc_feature
<222> LOCATION: (157)..(204)
<223> OTHER INFORMATION: G10L
<220> FEATURE:
<221> NAME/KEY: misc_feature
<222> LOCATION: (205)..(249)
<223> OTHER INFORMATION: 14 aa of GFP

<400> SEQUENCE: 19
ggaattcact cccccaccac gatcgaacgg gaatggatag gaggcttgtg ggattgacgt    60
gatagggtag ggttggctat actgctggtg gcgaactcca ggctaataat ctgaagcgca   120

```
tggatacaag ttatccttgg aaggaaagac aattccggat cctgtagaaa taattttgtt      180
taactttaag aaggagatat acccatgggt aaaggagaag aacttttcac tggagttgtc      240
ccaagcatg                                                              249

<210> SEQ ID NO 20
<211> LENGTH: 22
<212> TYPE: DNA
<213> ORGANISM: Artificial
<220> FEATURE:
<223> OTHER INFORMATION: synthetic construct

<400> SEQUENCE: 20
tgaaatagat cttgatacga tc                                               22

<210> SEQ ID NO 21
<211> LENGTH: 20
<212> TYPE: DNA
<213> ORGANISM: Artificial
<220> FEATURE:
<223> OTHER INFORMATION: synthetic construct

<400> SEQUENCE: 21
gaattgggac aactccagtg                                                  20

<210> SEQ ID NO 22
<211> LENGTH: 20
<212> TYPE: DNA
<213> ORGANISM: Artificial
<220> FEATURE:
<223> OTHER INFORMATION: synthetic construct

<400> SEQUENCE: 22
tgaaaggcga gatcaccaag                                                  20

<210> SEQ ID NO 23
<211> LENGTH: 20
<212> TYPE: DNA
<213> ORGANISM: Artificial
<220> FEATURE:
<223> OTHER INFORMATION: synthetic construct

<400> SEQUENCE: 23
aagagaaaga gactccccag                                                  20

<210> SEQ ID NO 24
<211> LENGTH: 20
<212> TYPE: DNA
<213> ORGANISM: Artificial
<220> FEATURE:
<223> OTHER INFORMATION: synthetic construct

<400> SEQUENCE: 24
gcggaatctt ctactggtac                                                  20

<210> SEQ ID NO 25
<211> LENGTH: 20
<212> TYPE: DNA
<213> ORGANISM: Artificial
<220> FEATURE:
<223> OTHER INFORMATION: synthetic construct

<400> SEQUENCE: 25
gtacacgcaa gaaataggcc                                                  20
```

<210> SEQ ID NO 26
<211> LENGTH: 20
<212> TYPE: DNA
<213> ORGANISM: Artificial
<220> FEATURE:
<223> OTHER INFORMATION: synthetic construct

<400> SEQUENCE: 26
gttgtaggga gggacttatg                                               20

<210> SEQ ID NO 27
<211> LENGTH: 20
<212> TYPE: DNA
<213> ORGANISM: Artificial
<220> FEATURE:
<223> OTHER INFORMATION: synthetic construct

<400> SEQUENCE: 27
attgacttac tacaccccgg                                               20

<210> SEQ ID NO 28
<211> LENGTH: 26
<212> TYPE: DNA
<213> ORGANISM: Artificial
<220> FEATURE:
<223> OTHER INFORMATION: synthetic construct

<400> SEQUENCE: 28
gttcactggc gtggtcccaa tcctgg                                        26

<210> SEQ ID NO 29
<211> LENGTH: 25
<212> TYPE: DNA
<213> ORGANISM: Artificial
<220> FEATURE:
<223> OTHER INFORMATION: synthetic construct

<400> SEQUENCE: 29
tcatccatgc catgcgtgat cccag                                         25

<210> SEQ ID NO 30
<211> LENGTH: 26
<212> TYPE: DNA
<213> ORGANISM: Artificial
<220> FEATURE:
<223> OTHER INFORMATION: synthetic construct

<400> SEQUENCE: 30
cctgttcctt ggccaacact tgtcac                                        26

<210> SEQ ID NO 31
<211> LENGTH: 26
<212> TYPE: DNA
<213> ORGANISM: Artificial
<220> FEATURE:
<223> OTHER INFORMATION: synthetic construct

<400> SEQUENCE: 31
ccatgtgtaa tcccagcagc agttac                                        26

<210> SEQ ID NO 32
<211> LENGTH: 23
<212> TYPE: DNA
<213> ORGANISM: Artificial
<220> FEATURE:
<223> OTHER INFORMATION: synthetic construct

```
<400> SEQUENCE: 32
ggcagaagcg gtgatcgccg aag                                           23

<210> SEQ ID NO 33
<211> LENGTH: 28
<212> TYPE: DNA
<213> ORGANISM: Artificial
<220> FEATURE:
<223> OTHER INFORMATION: synthetic construct

<400> SEQUENCE: 33
gcctcaaata gatcctgttc aagaaccg                                      28

<210> SEQ ID NO 34
<211> LENGTH: 27
<212> TYPE: DNA
<213> ORGANISM: Artificial
<220> FEATURE:
<223> OTHER INFORMATION: synthetic construct

<400> SEQUENCE: 34
ctgggattac acatggcatg gatgaac                                       27

<210> SEQ ID NO 35
<211> LENGTH: 28
<212> TYPE: DNA
<213> ORGANISM: Artificial
<220> FEATURE:
<223> OTHER INFORMATION: synthetic construct

<400> SEQUENCE: 35
cgatacttcg gcgatcaccg cttctgcc                                      28
```

PLASTID TRANSFORMATION OF MAIZE

CROSS REFERENCE TO RELATED APPLICATIONS

This application is a continuation of U.S. application Ser. No. 11/244,263 filed Oct. 5, 2005, which is a divisional of U.S. application Ser. No. 10/248,492 filed Jan. 23, 2003, which claims priority to U.S. Application No. 60/319,095 filed Jan. 23, 2002, the contents of all of which are hereby incorporated in their entireties by reference into this application.

BACKGROUND OF INVENTION

This invention relates to the application of genetic engineering techniques to plants. Specifically, the invention relates to compositions and methods for transformation of nucleic acid sequences into plant cell plastids.

Molecular biological techniques have enabled researchers to introduce pieces of DNA from one organism to another organism. Such techniques, referred to as recombinant DNA technology, have positively impacted the areas of medicine and agriculture. Conventional cloning methods have enabled the introduction of new pharmaceuticals and improved crops of agricultural importance. As the need for the introduction of multiple pieces of DNA and larger fragments of DNA into numerous target hosts increases, the need for novel cloning strategies increases accordingly.

The plastids of higher plants are an attractive target for genetic engineering. Plant plastids (chloroplasts, amyloplasts, elaioplasts, chromoplasts, etc.) are the major biosynthetic centers that in addition to photosynthesis are responsible for production of industrially important compounds such as amino acids, complex carbohydrates, fatty acids, and pigments. Plastids are derived from a common precursor known as a proplastid and thus the plastids present in a given plant species all have the same genetic content. Plant cells contain 500-10,000 copies of a small 120-160 kilobase circular genome, each molecule of which has a large (approximately 25 kb) inverted repeat. Thus, it is possible to engineer plant cells to contain up to 20,000 copies of a particular gene of interest, which potentially can result in very high levels of foreign gene expression.

Plastid transformation has been restricted to a few dicot species. In all successful experiments (Svab et al., Proc. Natl. Acad. Sci. USA 87, 8526-8530, 1990; Svab and Maliga, Proc. Natl. Acad. Sci. USA 90:913-917, 1993; Sikdar et al., Plant Cell Reports 18:20-24, 1998; Sidorov et al., Plant Journal 19(2):209-216, 1999), green leaves that contain developed chloroplasts were the target material used for particle bombardment. The most efficient selectable marker for isolation of plastid transformants is aadA, which confers resistance to the antibiotics spectinomycin and streptomycin (Svab et al., Proc. Natl. Acad. Sci. USA 87, 8526-8530, 1990; Svab and Maliga, Proc. Natl. Acad. Sci. USA 90:913-917, 1993; Sikdar et al., Plant Cell Reports 18:20-24, 1998; Sidorov et al., Plant Journal 19(2):209-216, 1999). NPTII, conferring resistance to kanamycin, has been reported for tobacco (Carrer et al., Mol Gen Genet 241:49-56, 1993) and glyphosate (U.S. Patent Application 200242934) were also used for selecting plastid transformants.

Recently, plastid transformation in rice was reported using a nongreen embryogenic culture as initial material for transformation (Khan and Maliga, Nature Biotechnology 17(9): 910-915, 1999). Selection was for streptomycin resistance conferred by aadA, as rice is not sensitive to spectinomycin. Selection was applied for only two weeks in liquid suspension and during the subsequent plant regeneration phase. Regenerated plants were chimeric, with some leaves containing sectors with transformed plastids. However, the transformed cells were also apparently only heteroplasmic, having both transformed and non-transformed plastids. This pattern of heteroplasmy is most likely due to the short period of selection that did not allow enough time for amplification of transformed plastids prior to plant regeneration.

However, a need still exists for a method of producing homoplasmic monocotyledonous plants, which are most useful. The present invention should be applicable to all monocots.

SUMMARY OF INVENTION

Novel methods for producing transplastomic monocotyledonous plants are provided. Such methods employ novel combinations of starting explant material with an appropriate monocotyledonous optimized plastid transformation vector and selection/tissue culture protocols. The invention described herein provides a method for obtaining homoplasmic monocotyledonous plants. In preferred embodiments of the present invention, the explant is chosen from among green multiple bud cultures, greening embryogenic callus, dark-grown embryogenic callus, or pre-cultured immature embryos. Plant cells containing transformed plastids are identified and selected and the cells amplified. Transplastomic plants are regenerated therefrom. In a preferred embodiment, explants from maize tissue are used. The invention described herein provides transplastomic monocotyledonous plant cells and sectors. Also provided herein are monocotyledonous plants, including maize, rice and wheat, whose plastids are transformed to contain a heterologous nucleic acid sequence conferring a desired trait or outcome to the resulting transgenic plant.

BRIEF DESCRIPTION OF SEQUENCES

Figure 1:
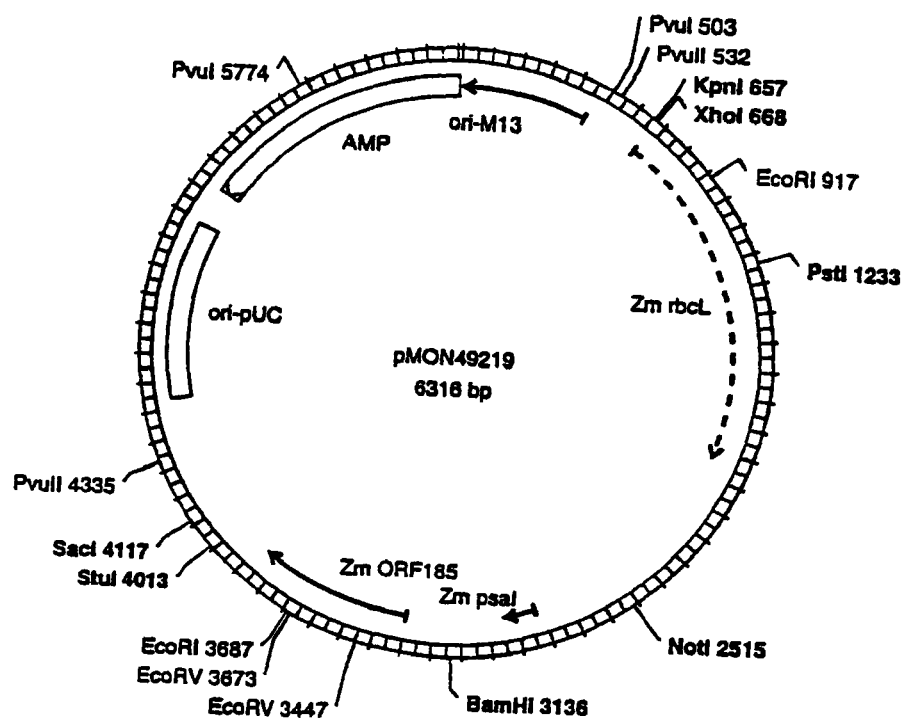
FIG. 1. Plasmid map of construct pMON49219.

SEQ ID NO:1 PCR primer Xu10
SEQ ID NO:2 PCR primer Xu11
SEQ ID NO:3 PCR primer Xu12
SEQ ID NO:4 PCR primer Xu13
SEQ ID NO:5 PCR primer Xu7
SEQ ID NO:6 PCR primer Xu8
SEQ ID NO:7 maize rbcL flanking region
SEQ ID NO:8 maize inverted repeat region
SEQ ID NO:9 PCR primer
SEQ ID NO:10 PCR primer
SEQ ID NO:11 PCR primer SEQ ID NO:12 PCR primer
SEQ ID NO:13 maize plastid promoter from rrn16
SEQ ID NO:14 maize Prrn with G10L
SEQ ID NO:15 termination region from tobacco rps16 gene
SEQ ID NO:16 tobacco Prrn with atpB gene leader plus DB
SEQ ID NO:17 termination region from maize petD gene
SEQ ID NO:18 termination region from maize rbcL gene
SEQ ID NO:19 maize Prrn plus G10L plus 14 aa of GFP
SEQ ID NO:20 PCR primer 10
SEQ ID NO:21 PCR primer 60
SEQ ID NO:22 PCR primer 61
SEQ ID NO:23 PCR primer 62
SEQ ID NO:24 PCR primer 63
SEQ ID NO:25 PCR primer 64
SEQ ID NO:26 PCR primer 65
SEQ ID NO:27-PCR primer 66
SEQ ID NO:28 PCR primer GFP 5':1
SEQ ID NO:29 PCR primer GFP 3':2
SEQ ID NO:30 PCR primer 202
SEQ ID NO:31 PCR primer 201
SEQ ID NO:32 PCR primer 198
SEQ ID NO:33 PCR primer 199
SEQ ID NO:34 PCR primer 200
SEQ ID NO:35 PCR primer 194

DETAILED DESCRIPTION

Definitions

In order to provide a clear and consistent understanding of the specification and the claims, including the scope given to such terms, the following definitions are provided.

A first nucleic acid sequence is "operably linked" with a second nucleic acid sequence when the sequences are arranged so that the first nucleic acid sequence affects the function of the second nucleic acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well known (see for example, Sambrook et al., Molecular Cloning: A Laboratory Manual, Cold Spring Harbor Press, 1989; Maliga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

Methods for chemical synthesis of nucleic acids are discussed, for example, in Beaucage and Carruthers (Tetra. Letts. 22:1859-1862, 1981) and Matteucci et al. (J. Am. Chem. Soc. 103:3185, 1981). Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Campbell et al., Plant Physiol. 92:1-11, 1990). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence that is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to, promoter regions, 5' untranslated leaders, introns, genes, 3' untranslated regions, and other regulatory sequences or sequences that affect transcription or translation of one or more nucleic acid sequences.

The terms "recombinant DNA construct," "recombinant vector," "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

As used herein, "recombinant" includes reference to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

By "host cell" is meant a cell that contains a vector and supports the replication, transcription, or transcription and translation (expression) of the expression construct. Host cells for use in the present invention can be prokaryotic cells, such as $E.\ coli$, or eukaryotic cells such as yeast, plant, insect, amphibian, or mammalian cells. Preferably, host cells are monocotyledenous plant cells.

As used herein, the term "plant" includes reference to whole plants, plant organs (for example, leaves, stems, roots, etc.), seeds, and plant cells and progeny of same. Plant cell, as used herein, includes, without limitation, seed suspension cultures, embryos, meristematic regions, callus tissue, leaves, roots, shoots, gametophytes, sporophytes, pollen, and microspores. The class of plants that can be used in the methods of the present invention is generally as broad as the class of higher plants amenable to transformation techniques, including monocotyledenous plants. Particularly preferred plants include barley, corn, oat, rice, rye, sorghum, sugarcane, triticale, and wheat.

As used herein, "transgenic plant" includes reference to a plant that comprises within its nuclear genome a heterologous polynucleotide. Generally, the heterologous polynucleotide is stably integrated within the nuclear genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "sector" refers to a proliferating lineage of cells in which exogenous DNA is stably integrated and inherited through organelle replication in daughter cells.

As used herein, "transplastomic" refers to a plant cell having a heterologous nucleic acid introduced into the plant cell plastid. The introduced nucleic acid may be integrated into the plastid genome or may be contained in an autonomously replicating plasmid. Preferably, the nucleic acid is integrated into the plant cell plastid's genome. A plant cell can be both transgenic and transplastomic.

The term "introduced" in the context of inserting a nucleic acid sequence into a cell, means "transfection" or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

The present invention describes a method for the production of a plastid transformant of maize using microprojectile bombardment of green, light-grown cultures. As target tissues, use of greening embryogenic cultures, dark-grown embryogenic cultures and pre-cultured immature embryos is also described. Successful plastid transformation includes several steps: a) engineering of plastid targeted constructs with an efficient selectable marker; b) establishment of regenerable cell cultures containing plastids suitable for transformation; c) development of a proper selection scheme favorable for sorting out of transformed plastids; and d) recovery of stable plastid transformants.

In developing the constructs of the invention, the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA that is employed in the regulatory regions or the nucleic acid sequences of interest for expression in the plastids. Methods for restriction digests, Klenow blunt end treatments, ligations, and the like are well known to those in the art and are described, for example, by Maniatis et al. (in Molecular cloning: a laboratory manual (1982) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation by joining or removing of sequences, linkers, or the like. Normally, the vectors will be capable of replication in at least a relatively high copy number in $E.\ coli$. A number of vectors are readily available for cloning, including such vectors as pBR322, pUC series, M13 series, and pBluescript (Strategene; La Jolla, Calif.).

The constructs for use in the methods of the present invention are prepared to direct the expression of the nucleic acid sequences directly from the host plant cell plastid. Examples of such constructs and methods are known in the art and are generally described, for example, in Svab et al. (1990) Proc. Natl. Acad. Sci. USA 87:8526-8530 and Svab and Maliga (1993) Proc. Natl. Acad. Sci. USA 90:913-917 and in U.S. Pat. No. 5,693,507.

The skilled artisan will recognize that any convenient element that is capable of initiating transcription in a plant cell plastid, also referred to as "plastid functional promoters," can be employed in the constructs of the present invention. A number of plastid functional promoters are available in the art for use in the constructs and methods of the present invention. Such promoters include, but are not limited to, the promoter of the D1 thylakoid membrane protein, psbA (Staub et al. EMBO Journal, 12(2):601-606, 1993), and the 16S rRNA promoter region, Prrn (Svab and Maliga, 1993, Proc. Natl. Acad. Sci. USA 90:913-917). The expression cassettes can include additional elements for expression of the protein, such as transcriptional and translational enhancers, ribosome binding sites, and the like.

As translation is a limiting step for plastid transgene expression, a variety of translational control elements need to be tested for efficacy. Efficient transgene translation will ensure that the markers used for selection of plastid transformed cells will function. Examples of such translational enhancing sequences include the heterologous bacteriophage gene 10 leader (G10L) (U.S. Pat. No. 6,271,444), the G10L including the downstream box (DB) (U.S. patent application Ser. No. 09/668,188), or the 14 amino acids from the green fluorescent protein (GFP) (U.S. patent application Ser. No. 09/351,124) enhancer elements.

Regulatory transcript termination regions may be provided in the expression constructs of this invention as well. Transcript termination regions may be provided by any convenient transcription termination region derived from a gene source, for example, the transcript termination region that is naturally associated with the transcript initiation region. The skilled artisan will recognize that any convenient transcript termination region that is capable of terminating transcription in a plant cell may be employed in the constructs of the present invention.

The expression cassettes for use in the methods of the present invention also preferably contain additional nucleic acid sequences providing for the integration into the host plant cell plastid genome or for autonomous replication of the construct in the host plant cell plastid. Preferably, the plastid expression constructs contain regions of homology for integration into the host plant cell plastid. The regions of homology employed can target the constructs for integration into any region of the plastid genome; preferably the regions of homology employed target the construct to either the inverted repeat region of the plastid genome or the large single copy region. Where more than one construct is to be used in the methods, the constructs can employ the use of the regions of homology to target the insertion of the construct into the same or a different position of the plastid genome.

Additional expression cassettes can comprise any nucleic acid to be introduced into a host cell plastid by the methods encompassed by the present invention including, for example, DNA sequences or genes from another species, or even genes or sequences that originate with or are present in the same species, but are incorporated into recipient cells by genetic engineering methods rather than classical reproduction or breeding techniques. An introduced piece of DNA can be referred to as exogenous DNA. Exogenous as used herein is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

A number of factors affect successful plastid transformation. Among them the most critical are 1) the target material used for delivering plastid-expressing genes into and regenerating transformants from and 2) the use of proper selectable markers and effective selection regimes. Green leaves, which contain large numbers of well-developed chloroplasts, are the ideal target material for introducing plastid-expressing foreign genes into plastids. In all successful stable plastid transformation reports to-date, green leaves are the only target material used because of the availability of well-established leaf-based plant regeneration systems in those species (tobacco, *Arabidopsis*, and potato). However, in corn, like most monocotyledonous plant species, plant regeneration from leaf tissue is impossible or very inefficient, which severely limits the possibility of using leaf tissue for corn plastid transformation. Instead, we have been using maize light- and dark-grown embryogenic cultures or immature embryos and light-grown green multiple bud cultures for plastid transformation. Immature embryos and embryogenic cultures derived from immature embryos are typically highly transformable using nuclear transformation approaches, but they contain immature plastids that may not be optimally suited for plastid transformation. Light-grown cultures are established by culturing embryogenic callus or excised meristem region from in vitro germinating seedlings on media containing different levels and different combinations of plant growth regulators under light and selecting for green and highly regenerable (either embryogenic or multiple bud) callus cultures. The light-grown cultures have been used for maize plastid transformation because of the presence of developing or developed chloroplasts and good plant regeneration capacity. However, these green cultures are more heterogeneous than embryogenic cultures and contain some developed tissues that are not highly transformable. The additional novel strategy of using greening embryogenic callus as the target material was developed because such cultures contain developing plastids that may be a more amenable target for plastid transformation, but also maintain the high transformation capacity normally attributed to embryogenic cultures. To select for plastid transformants following microprojectile bombardment, different selection regimes have been developed for the different target materials.

In addition, streptomycin or glyphosate selection with green multiple bud or greening embryogenic cultures could be more effective because identification of plant cells resistant to streptomycin relies on the green phenotype of resistant cells, and glyphosate selection could be most effective with the meristematic tissues, the natural sink for glyphosate. Green multiple bud corn cultures can be grown in many ways (U.S. Pat. No. 5,767,368; Zhong et al., 1996 Plant Physiol. 110:1097-1107), but any method that produces cells containing chloroplasts or their precursors can be utilized in this invention. The use of "greening embryogenic" cultures has not been reported. Several corn genotypes, including a triple hybrid (Pa91×H99)×A188, H99, Honey and Pearl, HiII and LH198×HiII were used in the following experiments. However, any corn genotype could be used by one of skill in the art.

Because plant cells contain a large copy number of plastid genomes, an effective selectable marker and selection regime are very important for selecting homoplasmic transformants. Selectable markers that have been used for plastid transformation include aadA, which confers resistance to the antibiotics spectinomycin and streptomycin, and the CP4 gene that confers resistance to the herbicide glyphosate. In the case of streptomycin, the antibiotic is not lethal to plant cells. Selection relies on green phenotype of resistant cells. In contrast, glyphosate is a plastid-lethal marker and destroys plastid membrane structure at the lethal concentration. Effective selection therefore may be facilitated by a sub-lethal selection scheme, as outlined in US Patent Application 200242934.

EXAMPLES

The following examples further illustrate the present invention. They are in no way to be construed as a limitation in scope and meaning of the claims.

Example 1

Vector Constructions

Plastid vectors optimally contain several critical elements: a highly expressed selectable marker, a reporter gene for easy screening and identification of transgenic plastids, and a transgene insertion site that does not negatively influence expression or function of the transgene or the neighboring endogenous plastid genes.

Insertion Sites:

Plastid vectors are designed to target transgene integration into the plastid genome via homologous recombination. The location of transgene insertion must be chosen such that the insertion does not cause any disruption of normal plastid function. This is achieved by cloning the transgenes into a plastid intergenic region where no open reading frames exist, preferably such that readthrough transcription from the transgenes into neighboring resident plastid genes is avoided. Two plastid genomic locations are targeted for insertion of transgenes: the Large Single Copy region and the Inverted Repeat region. Because the Inverted Repeat region is present in two copies per genome, the transgenes will also be present in two copies in transformed lines.

a) Large Single Copy Region

In tobacco, the site between the rbcL and accD genes in the tobacco Large Single Copy region was shown to be a successful insertion site (Svab and Maliga, 1992, ibid.). Based on success in tobacco, we also chose the maize plastid genomic region downstream of rbcL as the site of insertion for maize plastid transgenes. However, the gene order between tobacco and maize in this genomic region is different. Complete nucleotide sequencing of the maize plastid genome (Maier et al., 1995 J. Mol. Biol. 251:614-628; Genbank accession X86563) revealed that a large inversion occurred during evolutionary separation of the monocot and dicot plastid lineages such that the region downstream of rbcL is completely different between tobacco and maize. Therefore, insertion of transgenes in this region requires thoughtful identification of a suitable non-coding, intergenic region.

An ~3.4 kb region surrounding the maize plastid rbcL gene was cloned for use as a homologous targeting sequence to direct transgene insertion. First, an ~2.8 kb PstI/SpeI DNA fragment from plasmid pZmc301 (gift of Dr. Ralph Bock, Freiburg, Germany) that carries a portion of the rbcL coding region and downstream psaI and -orf185 genes was subcloned to create plasmid pMON49204. Then, a further subclone of pMON49204, an ~1 kb BamHI/PstI fragment, was generated and used as template for PCR mutagenesis to create an engineered NotI site used for subsequent insertion of plastid transgenes. The NotI site was created by overlap PCR mutagenesis using PCR primers (SEQ ID NO:1-4). The newly created NotI site and surrounding region was verified by sequencing and then reinserted back into pMON49204 as a BamHI/PstI fragment, to create plasmid pMON49206. Lastly, an additional ~560 bp of homologous flanking sequence, carrying a further portion of the maize rbcL gene, was PCR amplified from total maize genomic DNA using PCR primers (SEQ ID NO:5-6). The amplified fragment was cloned next to pMON49206 to create the Single Copy Region transformation vector pMON49219 (FIG. 1). The nucleotide sequence of the cloned ~3.4 kb region is shown in SEQ ID NO:7.

Translation of the ~3.4 kb sequence in all six possible reading frames identified the known rbcL, psaI and orf185 genes. In addition, several small open reading frames of less than 50 amino acids were identified. To facilitate cloning of transgenes into the homologous flanking region, the unique NotI restriction site was engineered ~580 bp downstream of rbcL in the rbcL-psaI intergenic region, away from any small open reading frames. The NotI insertion site is flanked by ~1.5 kb and ~1.8 kb of homologous DNA on either side of the transgenes to direct integration into the plastid genome by homologous recombination. Plasmid pMON49219 shown in FIG. 1 carries this ~3.4 kb plastid fragment with the engineered NotI site.

b) Inverted Repeat Region

The second targeting location for insertion of maize transgenes is upstream of trnV, in the intergenic region between the trnV/rrn16 operon and the divergently transcribed rps12/3"-rps7 operon. This region is located in the Large Inverted Repeat region and is therefore present in two copies per plastid genome. The analogous region is routinely used for transgene insertion in tobacco (Staub and Maliga, 1993; Zoubenko et al., 1994 Nucleic Acids Res. 22:3819-3824). However, the sequence and gene content at the site of insertion differs between tobacco and maize.

Figure 2:
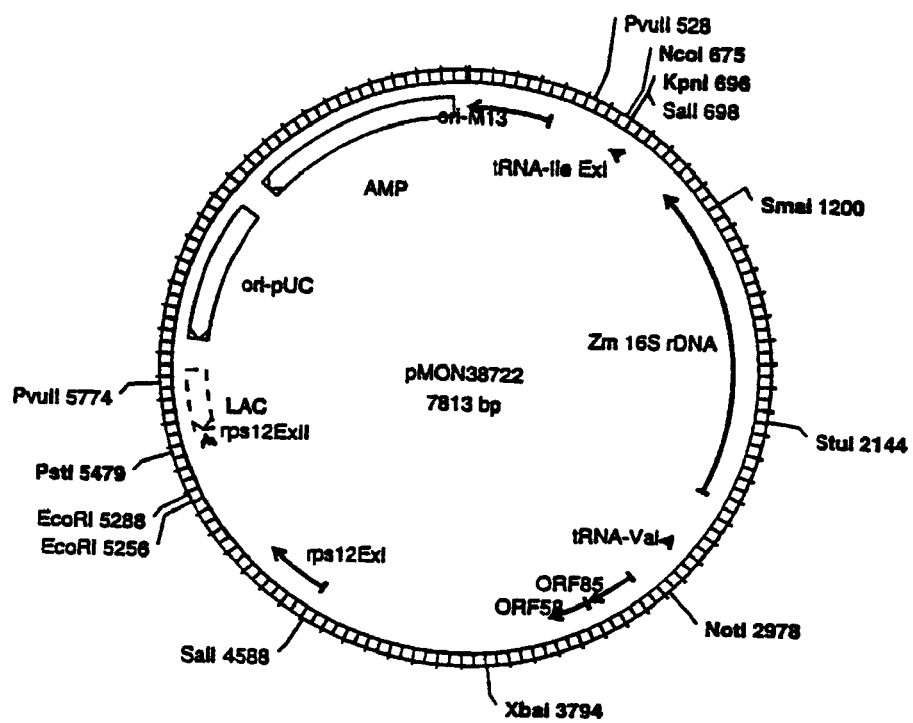
FIG. 2. Plasmid map of construct pMON38722.

An ~4.8 kb plastid DNA fragment was chosen for PCR amplification and cloning as the maize homologous flanking region. The sequence of the fragment is shown in SEQ ID NO:8. For amplification of the rrn16/trnV gene flanking region, one PCR primer (5'-gggtaccgtcgacttat-cagggggcgcgctctaccactgagctaatagccc-3') (SEQ ID NO:9) was designed after the trnI gene coding region that lies downstream of the rrn16 gene. Note that sites for the restriction enzymes KpnI and SalI were incorporated to the end of the PCR primer for subsequent cloning purposes. The second PCR primer (5'-taagcttgcggccgcccggttgacaat-tgaatccaatttttcccattatttgac-3') (SEQ ID NO:10) was designed to anneal in the rrn16/trnV-rps12/3'-rps7 intergenic region and also encodes a unique engineered NotI restriction site (underlined). For amplification of the rps12/3"-rps7 gene flanking region, one primer was designed after a part of the rps7 gene coding region (5'-aactagtcccgggccaccatgttaac-taatcgattacgaaaaattggatcgg-3') (SEQ ID NO:11). Note that SpeI and SmaI sites were incorporated onto the end of the PCR primer for subsequent cloning purposes. The second primer was designed to also anneal in the same location in the rrn16/trnV-rps12/3'-rps7 intergenic region, and also encode the unique NotI site (5'-ggaattcgcggccgctcctatcgaaaat-aggattgactatggattcgagcc-3') (SEQ ID NO:12). As a result of the PCR amplifications, the unique NotI insertion site was created approximately mid-way between the ~4.8 kb homologous flanking region, with ~2.3 kb and ~2.5 kb of homologous DNA on either side of the transgene insertion site. The pMON38722 clone with this maize flanking region and unique NotI site is shown in FIG. 2.

In tobacco, the transgene insertion site in the analogous region of the plastid genome disrupts an open reading frame of no known function that is not found in other plant species. Insertion into this location in tobacco has no deleterious effect (Staub and Maliga, 1992, ibid.). In maize, two different unidentified open reading frames, each with no known function, are present in the analogous position. Therefore, it is unknown whether insertion into these open reading frames would affect plastid gene functions. To avoid any possible effect on plastid gene function, the insertion site was chosen in the intergenic region between the trnV gene and the nearby ORF85 gene, away from any putative plastid gene regulatory elements.

Selectable Markers:

For selection of plastid transformed cells, the aadA gene that gives resistance to spectinomycin and streptomycin or the CP4 gene that confers tolerance to glyphosate was chosen.

For plastid transformation vectors carrying aadA, streptomycin was used as the selective agent because maize plastids are naturally resistant to spectinomycin. Selection using this antibiotic is based on inhibition of plastid protein synthesis, which prevents accumulation of photosynthetic proteins and chlorophyll, thus resulting in bleaching. Resistant cells are identified by their green color on selective media. Therefore, this antibiotic can only be used with light-grown, chlorophyll-containing green tissue culture systems.

Glyphosate is also used as a selective agent. Glyphosate inhibits aromatic amino acid biosynthesis but also has more pleiotropic effects including bleaching and inhibition of growth. Resistant cells are differentiated by growth and by greening if grown in the light. Therefore, this selectable marker is useful for both dark-grown or light-grown tissue culture systems.

Based on observations with glyphosate selection in tobacco, most selection regimes have focused on transitions from sub-lethal to lethal concentrations of the selective agent. Selection using this approach has been described in US Patent Application 200242934. It is also possible to use a steady-state concentration of glyphosate throughout the selection period, enough to inhibit growth of cells in culture but only gradually become lethal.

Transgene Expression Elements:

For expression of the aadA or CP4 transgenes, expression signals that provide for constitutive transcription and translation of the transgene are most desirable. The expression signals need to be derived from resident maize plastid genes to ensure that the appropriate trans-acting factors are present for faithful gene expression. In most cases, we have used the maize 16S ribosomal RNA (rrn16) operon promoter (ZmPrrn) (SEQ ID NO:13) to drive transgene expression. This promoter region includes the mapped transcriptional start site of the rrn16 operon (Strittmatter et al., 1985, EMBO J, 4 (3): 599-604).

For translation, several different elements are being tested. The plastid atpB gene leader and first 14 amino acids of its coding region (gift of Dr. Pal Maliga), fused to the ZmPrrn, are being tested. The encoded b-subunit of plastid ATPase accumulates in all plastid types, therefore it was predicted that the atpB gene leader would provide for constitutive translation. Furthermore, the 14-amino acid translational fusion was shown to enhance translation in some cases (Pal Maliga, personal communication).

The heterologous bacteriophage T7 gene 10 leader (G10L) is also being tested. This element has been shown to enhance translation in plastids (Staub et al., 2000 Nature Biotech. 18:333-338; U.S. patent application Ser. No. 09/113,690). In some cases, an additional translational fusion of 14 amino acids of the green fluorescent protein (14aaGFP), that has also been shown to enhance translation (U.S. patent application Ser. No. 09/351,124), is used in addition to the G 10L. In other cases, the "downstream box" sequence from the bacteriophage T7 gene 10 coding region (EC DB), which also enhances translation (U.S. patent application Ser. No. 09/668,188), is used in addition to the G10L.

Screenable Marker:

To facilitate identification of maize plastid transformants, a GFP transgene was included in the transformation vectors. GFP can be monitored in live tissue and used to follow the growth of transplastomic sectors (Sidorov et al. 1999 Plant Journal 19:209-216; U.S. patent application Ser. No. 09/351,124). The GFP transgene was also driven by the ZmPrrn promoter. The translational enhancer sequence, G10L (Staub et al., 2000, ibid.) was included to ensure constitutive high level translation.

Figure 3:
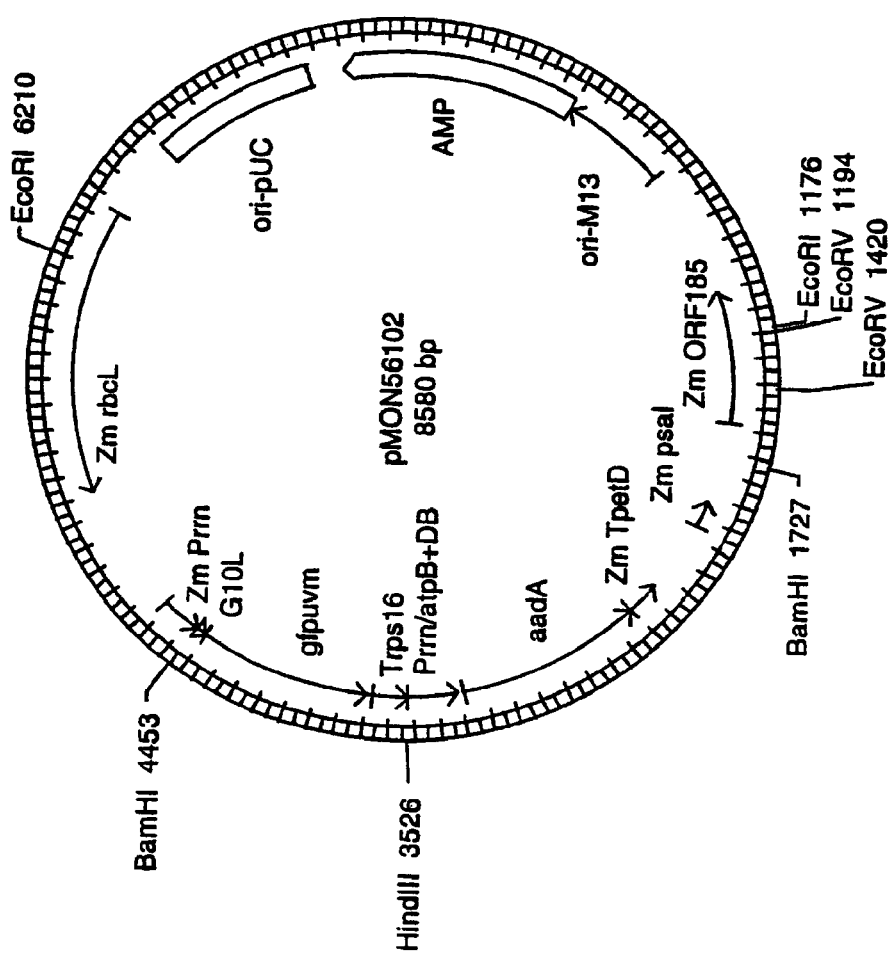
FIG. 3. Plasmid map of construct pMON56102.
Figure 5:
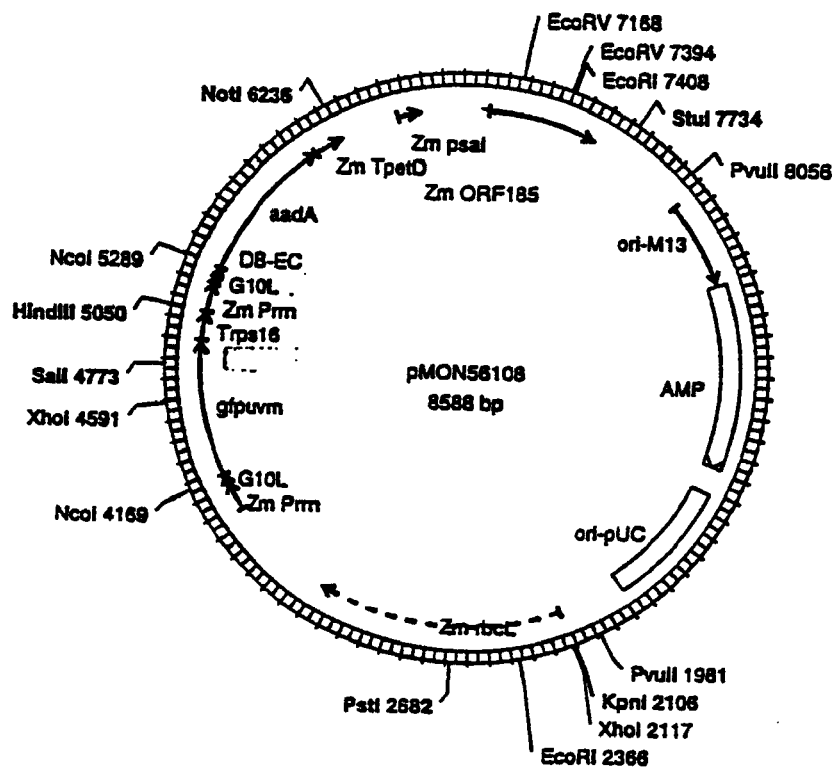
FIG. 5. Plasmid map of construct pMON56108.
Figure 6:
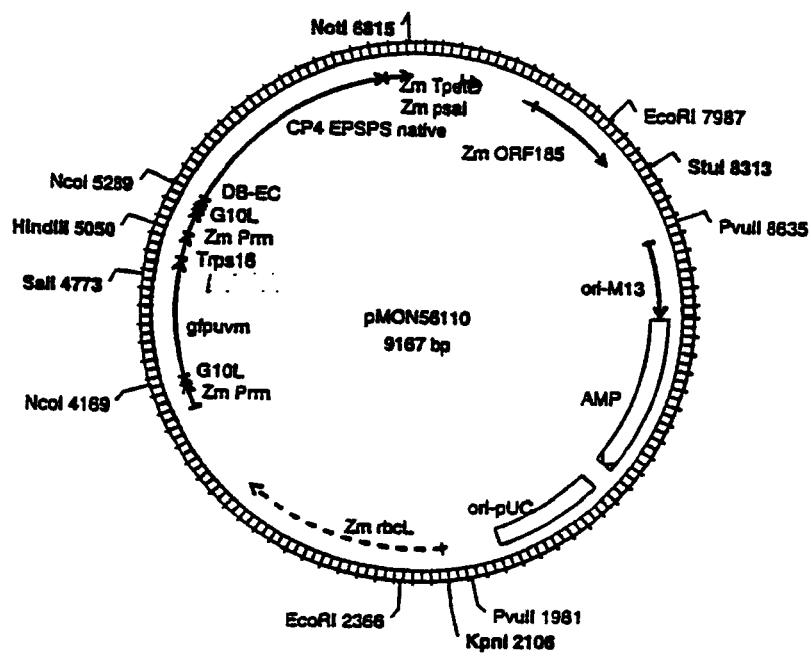
FIG. 6. Plasmid map of construct pMON56110.
Figure 7:
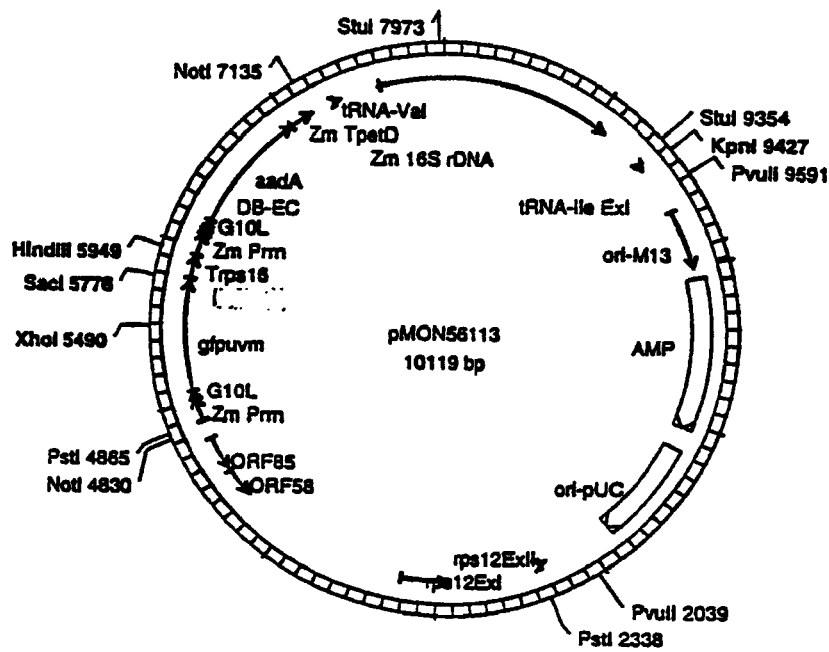
FIG. 7. Plasmid map of construct pMON56113.
Figure 8:
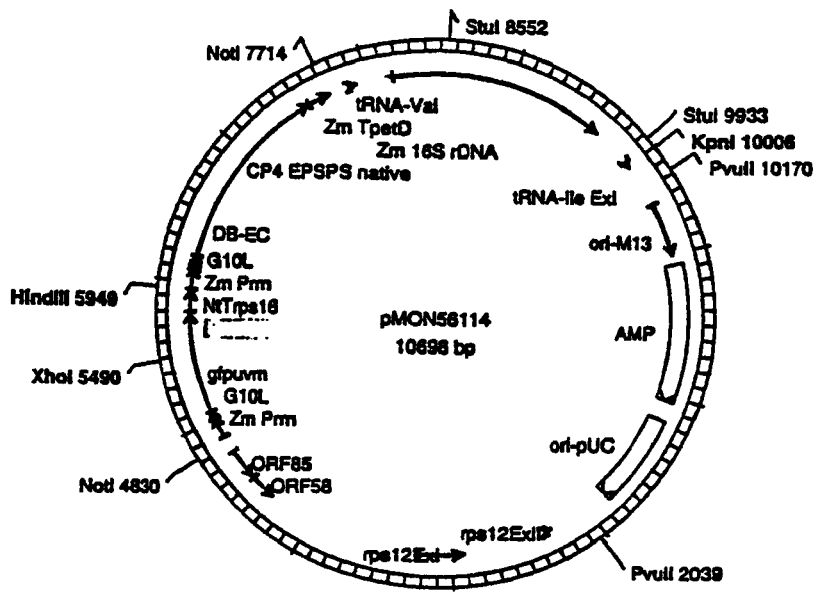
FIG. 8. Plasmid map of construct pMON56114.

Plastid Vectors:

pMON49219 (FIG. 1): maize genes rbcL, psaI and ORF185 Large Single Copy flanking region clone, including the unique NotI site used for transgene insertion.

pMON38722 (FIG. 2): maize genes rrn16 (16S rDNA), trnV (tRNA-Val), -ORF85 ORF58, and rps12 Exons I and II in the Inverted Repeat flanking region clone, including unique NotI site used for transgene insertion.

pMON56102 (FIG. 3): ZmPrrn.G10L (SEQ ID NO:14): GFP:NtTrps16 (SEQ ID NO:15) plus NtPrrn.atpB+DB (SEQ ID NO:16): aadA:ZmTpetD (SEQ ID NO:17) in the same direction as the rbcL gene in the pMON49219 flanking region.

pMON49296 (FIG. 4): ZmPrrn:GFP:ZmTrbcL (SEQ ID NO:18) plus ZmPrrn-.G10L:14aaGFP (SEQ ID NO: 19) -aadA: ZmTpetD in the same direction as the rbcL gene in the pMON49219 flanking region.

pMON56108 (FIG. 5): ZmPrrn.G10L:GFP:NtTrps16 plus ZmPrrn.G10L:EC DB-aadA:ZmTpetD in the same direction as the rbcL gene in the pMON49219 flanking region.

pMON56110 (FIG. 6): ZmPrrn:GFP:ZmTrbcL plus ZmPrrn.G10L:EC DB-CP4-:ZmTpetD in the same direction as the rbcL gene in the pMON49219 flanking region.

pMON56113 (FIG. 7): ZmPrrn.G10L:GFP:NtTrps16 plus ZmPrrn.G10L:EC DB-aadA:ZmTpetD upstream and in the same direction as the rrn16 gene in the pMON38722 flanking region.

pMON56114 (FIG. 8): ZmPrrn.G10L:GFP:NtTrps16 plus ZmPrrn.G10L:EC DB-CP4:ZmTpetD upstream and in the same direction as the rrn16 gene in the pMON38722 flanking region.

Nuclear Transformation Vectors

Figure 9:
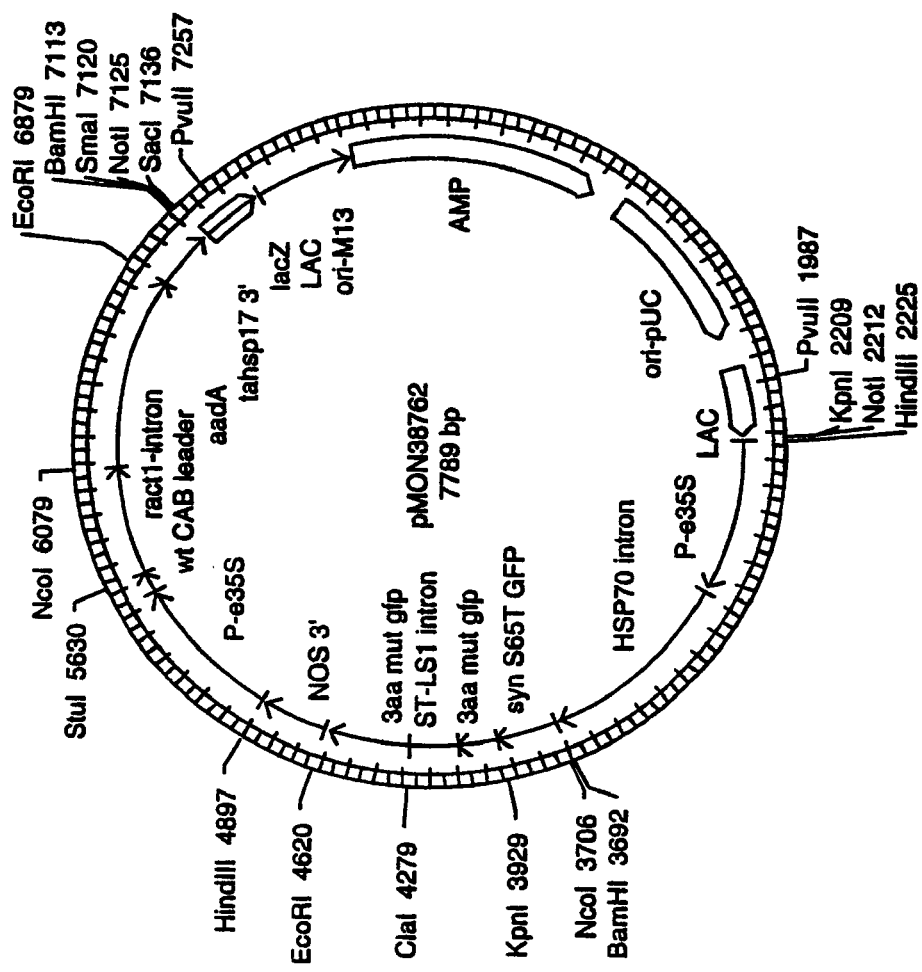
FIG. 9. Plasmid map of construct pMON38762.
Figure 11:
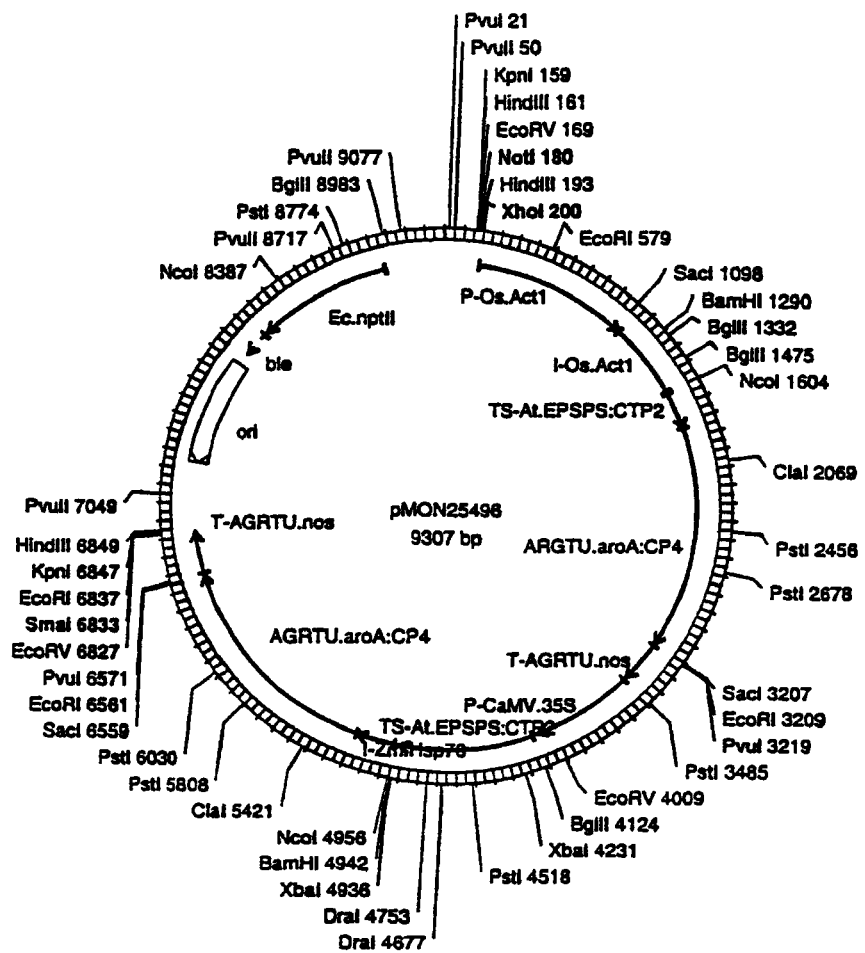
FIG. 11. Plasmid map of construct pMON25496.
Figure 12:
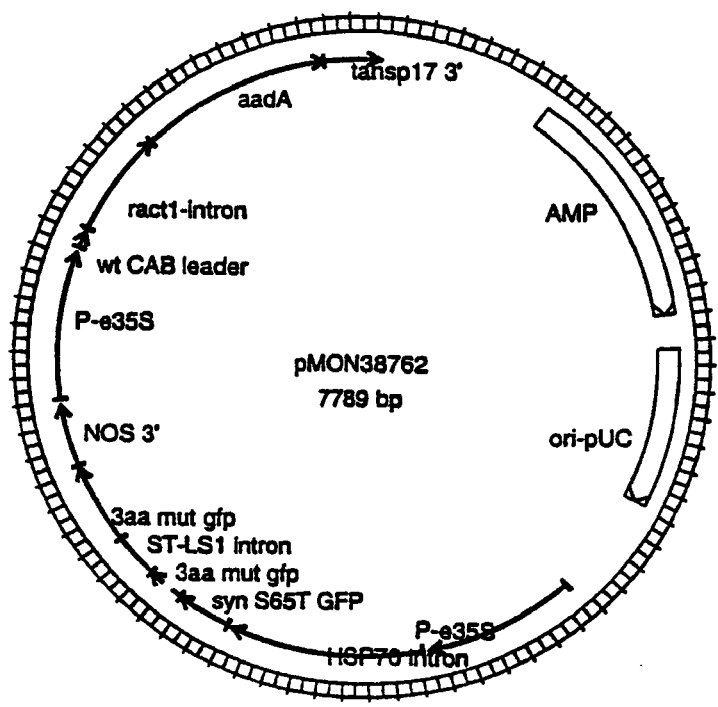
FIG. 12. Plasmid map of construct pMON38762.
Figure 13:
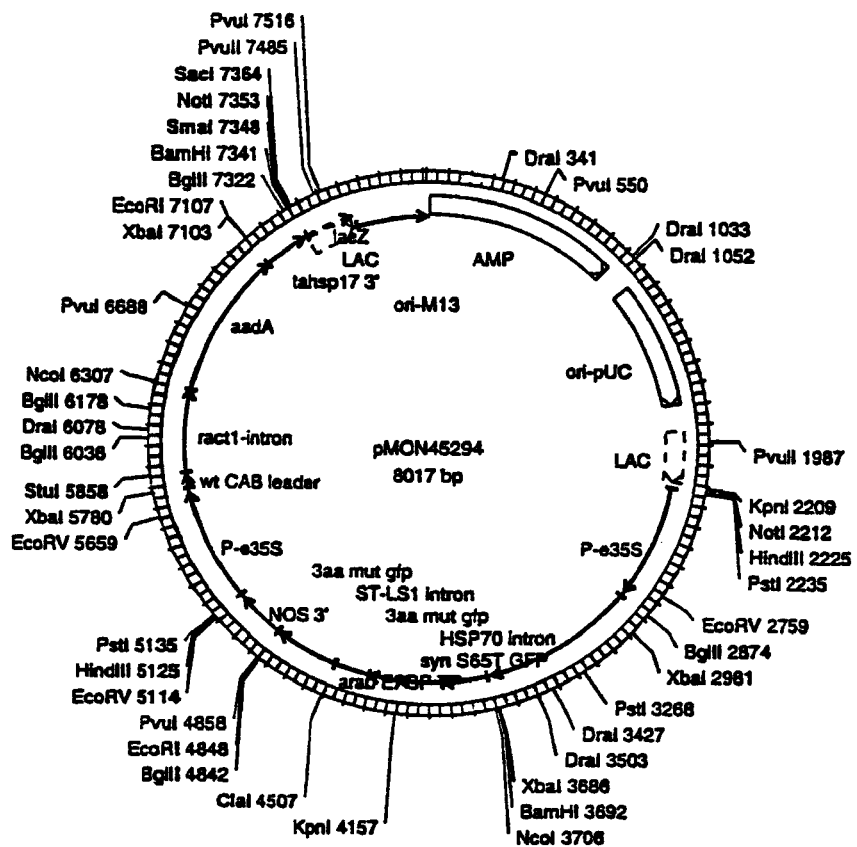
FIG. 13. Plasmid map of construct pMON45294.

Control nuclear transformations are valuable to determine ideal selection conditions and frequency of transformation using new maize explant types. Furthermore, transient nuclear expression of reporter genes can assist in developing optimal bombardment parameters. For these reasons, nuclear transformation vectors are routinely employed: pMON38762 (FIG. 9): GFP (green fluorescent protein) gene containing the hsp70 intron, driven by the 35S promoter and the nos3' terminator plus the streptomycin resistance gene (aadA) containing the rac intron, driven by the 35S promoter and the hsp17 3' terminator.

pMON30098 (FIG. 10): GFP gene driven by e35S promoter and HSP70 intron and nos 3"-terminator.

pMON25496 (FIG. 11): CP4 gene with *Arabidopsis* EPSPS chloroplast transit peptide driven by rice actin promoter and rice actin intron plus CP4 gene with *Arabidopsis* EPSPS chloroplast transit peptide driven by 35S promoter with maize HSP70 intron.

pMON38762 (FIG. 12): aadA gene driven by e35S promoter with cab gene leader and rice actin intron plus GFP gene driven by e35S promoter and HSP70intron.

pMON45294 (FIG. 13): aadA gene driven by e35S promoter with cab gene leader and rice actin intron plus GFP gene with *Arabidopsis* EPSPS chloroplast transit peptide driven by e35S promoter and HSP70intron.

Example 2

Initiation and Establishment of Green Multiple Bud Cultures as Target Materials

Plant Materials:

For the present invention, plants of hybrids Pa91×H99 were grown in a greenhouse or in the field with normal growth conditions for maize plants. Plants of Pa91×H99 were pollinated with pollen from line A188 plants to form embryos with genotype of (Pa91×H99)×A188 (also known as triple hybrid, or PHA). The hybrid ears were harvested approximately 10 days after pollination. Immature embryos were isolated the same day when the ears were harvested or after the ears were stored in a refrigerator (4° C.) for one to several days.

Establishment of Light-Grown Green Multiple Bud Cultures:

Green multiple bud cultures (also sometimes called green meristematic cultures) can be established from a variety of tissues. In some cases, green multiple bud cultures are established from dark-grown embryogenic callus that is transferred to light and maintained for several subcultures on MS2 or MS3 medium (Table 1), transferring green meristematic zones at each subculture until a homogeneous callus is established. For the present invention, the meristematic regions of young seedlings derived from immature embryos were used to establish the green multiple bud callus cultures as described below.

Immature embryos of H99 or (Pa91×H99)×A188 were isolated from sterilized ears and placed on CM4C medium (Table 2) with scutellum side touched to medium. The embryos were kept in the light culture room or Percival incubator (16-h light and 8-h dark, 27° C.). In 5-7 days the growing seedlings were approximately 1-3 cm long. A section (approximately 5 mm long) containing the nodal region (with apical meristem and leaf primordia) was dissected and laid horizontally on MS2 or MS3 medium. Initially the primary shoots continued to elongate and were trimmed weekly. Eventually, the meristematic regions enlarged and formed clusters of shoots/shoot primordia in approximately 6 weeks. The cultures were green, highly regenerable and considered meristematic. They were proliferated and maintained under the same growth conditions by breaking into smaller pieces and transferring onto fresh medium every 3-4 weeks. The cultures on MS2 and MS3 media were similar morphologically, except that the cultures were more compact on MS2 and more differentiated on MS3.

TABLE 1

Media used for inducing organogenic cultures from embryogenic callus cultures and meristem region.

| Medium | Reference and description of the medium |
|---|---|
| MS2 | MS medium (Murashige and Skoog, 1962 Physiol. Plant 15:473-479) supplemented with 40 g/l maltose, 500 mg/l casein hydrolysate, 1.95 g/l MES, 2 mg/l BA, 0.5 mg/l 2,4-D, 100 mg/l ascorbic acid, pH 5.8. |
| MS3 | The same as MS2, except that BA is 1 mg/l and 2,4-D is replaced by 2.2 mg/l picloram. |

TABLE 2

Callus induction media used for inducing callus from immature embryos.

| Embryo genotype | Callus induction medium | Reference and description of the medium |
|---|---|---|
| H99 (Pa91xH99)xA188 | CM4C | Cheng et al., 1997 Plant Physiol. 115:971-980. |
| LH198xHiII HiII | N6 1-100-12 | N6 medium supplemented with 1.38 g/L proline, 100 mg/L casein hydrolysate, 20 μM silver nitrate, 1 mg/L 2,4-D, 0.125 mg/L Cu, 0.125 mg/L Co and 1.25 mg/L Mo. |

In some cases, the genotype Honey and Pearl was used. In this case, mature seeds were purchased from a commercial source, surface sterilized and then placed on MSOD medium (MS medium with 40 g/L maltose, 20 g/L glucose, 150 mg/L asparagine, 100 mg/L inositol, 0.65 mg/L niotinic acid, 125 mg/L pyridoxine, 125 mg/L thiamine, 125 mg/L pantothenate, and 7 g/L Phytagar) and germinated in the dark for 4 days. After 4 days, the meristem region is excised about 3 mm below and 2 mm above the nodal area. The explants are then placed standing up in MS3 media containing 1 mg/L BAP and 2.2 mg/L picloram in the light at 26° C. for 18 hr of light. Primary shoots are then trimmed every 3-4 days until multiple buds are visible (about 3-4 weeks). At this time, the leaves on top of the buds are trimmed off, the buds are separated and then subcultured every three weeks.

DNA Delivery by Particle Gun Bombardment

Preparation of Target Materials for Bombardment

Actively proliferating meristematic areas from the green callus were selected, and leaves or leaf primordia were removed from one to a few days prior to particle gun bombardment. The selected calli were then transferred into the middle of the plates with solid MS3 or MS2 medium. The prepared plates were incubated at light conditions.

Precipitation of Plasmid DNA with Particles and Bombardment:

The plasmid DNA was precipitated with gold (0.4 or 0.6 μm) or tungsten particles according to standard operation procedure for helium gun. Particles (0.5 mg) are sterilized with 100% ethanol, washed 2-3 times each with 1 mL aliquots of sterile water. They are then resuspended in 500 μL of sterile 50% glycerol. Twenty-five μL aliquots of particle suspension are added into 1.5 mL sterile microfuge tubes, followed by 5 μL of DNA of interest (at 1 mg/mL) and mixing by finger-vortexing. A fresh $CaCl_2$ and spermidine premix is then prepared by mixing 2.5M $CaCl_2$ and 0.1M spermidine at a ratio of 5 to 2. Thirty-five μL of the freshly prepared "premix" is added to the particle-DNA mixture, and mixed quickly by finger-vortexing. The mixture is incubated at room temperature for 20 min. The supernatant is removed after a pulse spin in the microfuge. The DNA-particles mixture is washed twice, first by resuspending in 200 μL of 70% ethanol, followed by pulse spin and removing of the supernatant, repeated with 200 μL of 100% ethanol. The DNA-particles mixture is finally resuspended in 40 μL of 100% ethanol. After thorough mixing, an aliquot of 5 μL is loaded onto the center of the macrocarrier already installed in the macrocarrier holder, and allowed to dry in a low humidity environment, preferably with desiccant. Each tube can be used for 5-6 bombardments.

In comparison to standard protocol, double the concentration of DNA was also used for particle preparation. The plate with the target tissue was bombarded twice using the helium gun (Bio Rad, Richmond, Calif.) using the protocol described by the manufacturer, at target shelf levels L3. The gap distance was set at 1.0 cm and the rupture pressures at 1100-1550 psi.

Selection of Plastid Transformants in Green Multiple Bud Cultures Using aadA as a Selectable Marker DNA vector pMON56102 (FIG. 3) containing aadA and gfp genes (see Example 1) was used to bombard the (Pa91× H99)×A188 target tissues. After bombardment, the material remained on the same medium overnight (16-20 h) in the light culture room or in a Percival incubator. They were then transferred onto selection medium of MS3 with 100 mg/L streptomycin. The cultures were transferred onto fresh selection medium every 3-4 weeks until highly resistant callus colonies or sectors were observed or all the cultures were dead. During selection, the cultures were examined periodically under a Leica MZ80 GFP plus fluorescence microscope for GFP expression.

MS3 medium with 100 mg/L streptomycin was used for selection. Twenty-two plates with light-grown (Pa91×H99)×

A188 multiple bud culture were shot with pMON56102. After 4 weeks of selection, all plates were analyzed. In one plate a leaf arising directly from callus tissue with a positive GFP sector was observed. This leaf was sectored, having a linear green (streptomycin resistant) sector surrounded by white (streptomycin sensitive) sectors oriented from the base to the tip of the leaf, although the green sector made up the bulk of this leaf. Using fluorescence microscopy, GFP positive cells were identified from the base to the tip of the leaf located around the midvein of the leaf, coincident with the location of the green sector. The remainder of the leaf, coincident with the location of the white sectors, had red fluorescence due to the chlorophyll autofluorescence in untransformed cells.

Samples were also analyzed by laser scanning confocal microscopy. In control nuclear transformants expressing a non-targeted GFP gene, the GFP fluorescence is distributed all over the cytoplasm. The chloroplasts emit only red autofluorescence. The analysis of the putative transformed leaf confirmed that GFP fluorescence is localized in chloroplasts within the green sector. Confocal microscopy also confirmed that the recovered transformant is chimeric, carrying mostly homoplasmic cells in the green sector, but also some heteroplasmic cells at the junction between the green and white sectors.

The multiple bud callus with a small GFP positive area was transferred to selective medium with 50 mg/L streptomycin in an effort to amplify the transformed tissues. Although these cells and sectors did not regenerate into whole plants, it is expected that a plant could be regenerated from the protocol. More cells and sectors need to be obtained and evaluated.

Molecular Analysis of the Transformation Event

A small portion of the transformed leaf sector was sacrificed for DNA extraction and used for PCR analysis. The corn leaf sample was ground in 150 μL of CTAB and incubated at 65° C. for 30 min. The mixture was then cooled to room temperature and extracted with 150 μL of chloroform:isoamyl alcohol (24:1). The mixture was spun at 14,000 rpm for 10 min. The supernatant was collected to the new tube and two volumes of 100% ethanol were added. The solution was then kept at –20° C. for 30 min to precipitate the nucleic acids. DNA was spun down at 14,000 rpm for 10 min. The DNA pellet was then washed with 75% ethanol, air dried, and dissolved in 24 μL of water.

PCR reactions were performed using Roche Expand Long Template PCR System. Two microliters of the above DNA solution was used as the template. The other components were used according to the manufacturer's recommendations. The PCR mixture was first denatured at 94° C. for 2 min, then repeated 35 cycles of 94° C. for 10 sec, 53° C. for 30 sec and 68° C. for 2 min, and at last elongated at 68° C. for 10 min. The PCR products were then separated on 1% agarose gel.

Figure 14:
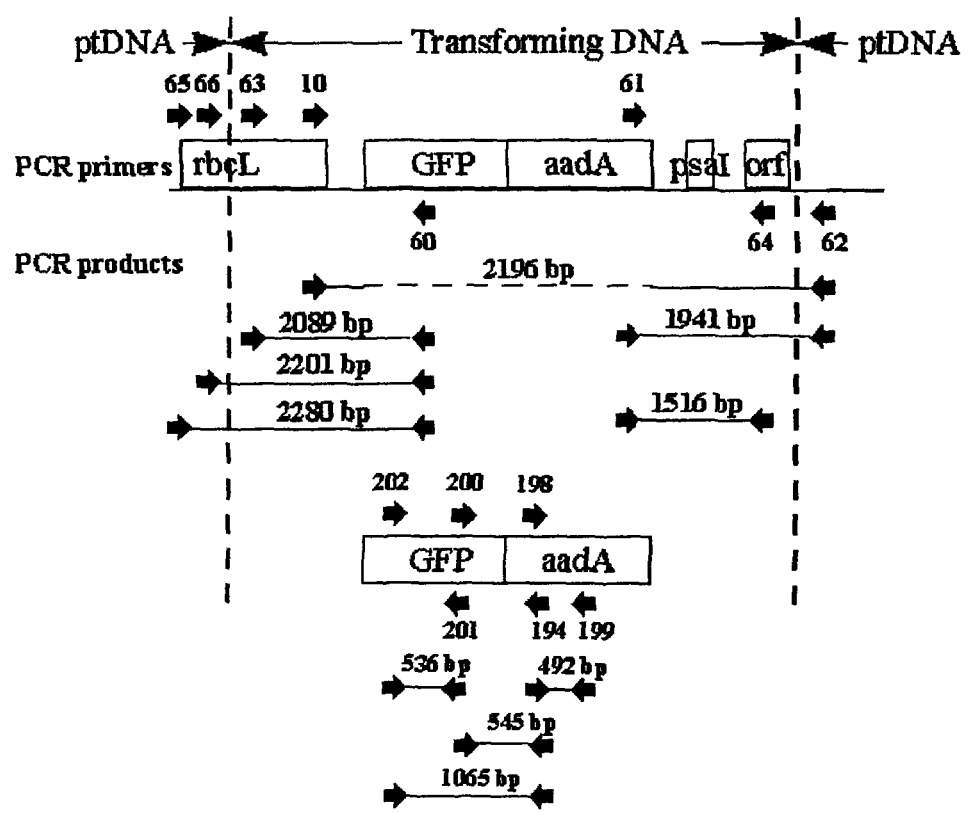
FIG. 14. Map of expected PCR products.

FIG. 14 shows the PCR primers used and the expected length of DNA products. The vertical dashed line indicates the junction of the foreign DNA insert on the transforming DNA and the flanking wild-type plastid DNA (ptDNA). The results show that the transforming DNA has integrated into the maize plastid genome. Specifically, the PCR 61/PCR62 (SEQ ID NO:22 and SEQ ID NO:23), PCR60/PCR65 (SEQ ID NO:21 and SEQ ID NO:26), and PCR60/PCR66 (SEQ ID NO:21 and SEQ ID NO:27) reactions show the predicted bands of 1941, 2280, and 2201 bp, respectively, that are only possible if the foreign DNA has integrated into the correct genomic location. The other PCR products show that the various portions of the transforming DNA are also intact, as expected for a homologous integration event.

A further experiment using a green multiple bud explant has produced at least one plastid transformed callus. The experiment utilized light-grown (Pa91×H99)'A188 multiple bud culture maintained on MS3 medium.

Figure 4:
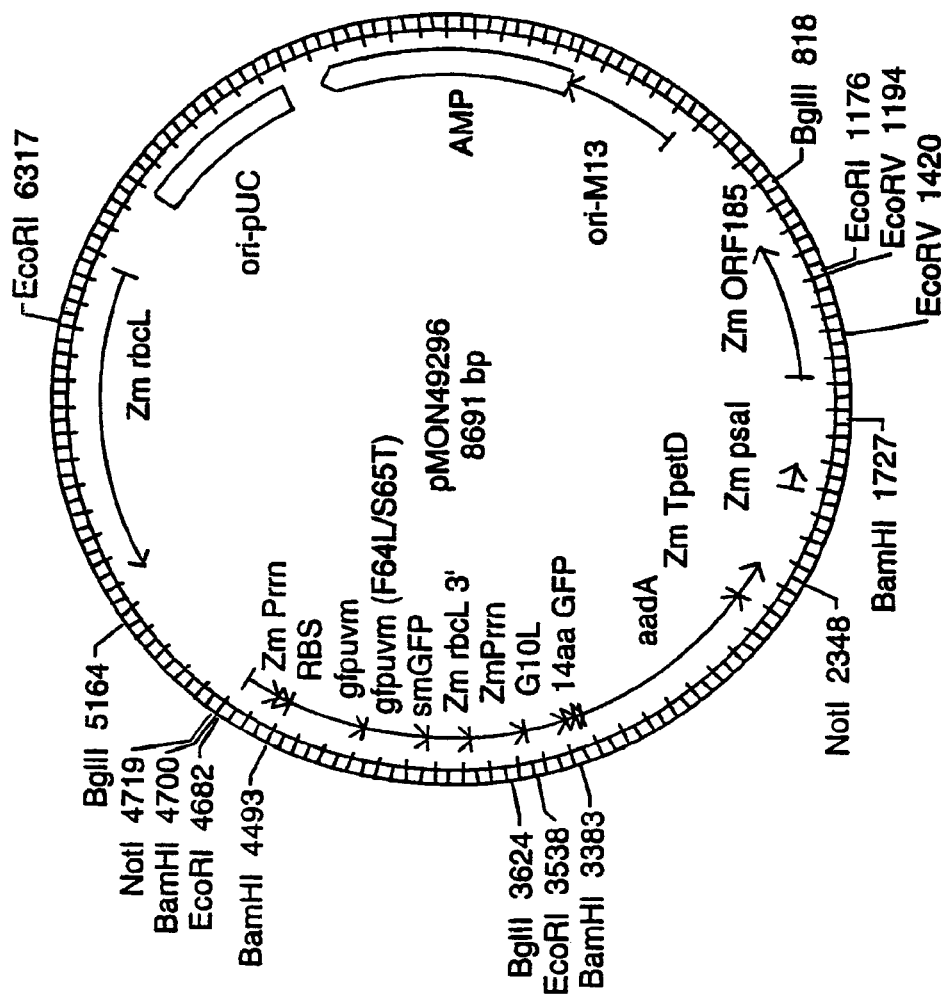
FIG. 4. Plasmid map of construct pMON49296.
Figure 10:
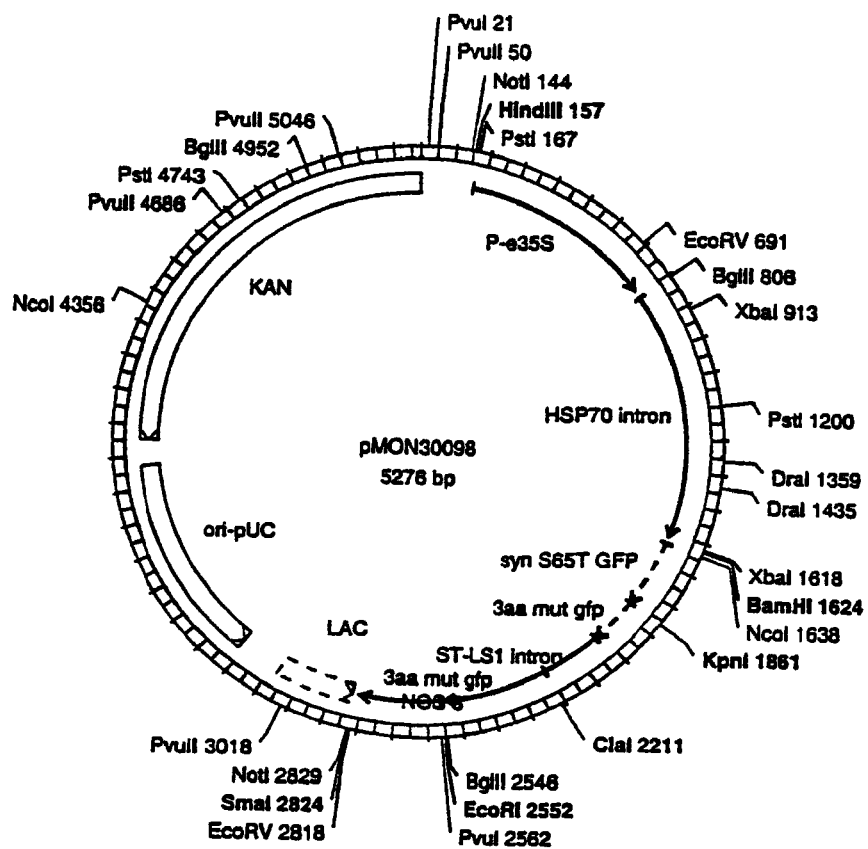
FIG. 10. Plasmid map of construct pMON30098.

In this experiment, a cobombardment protocol was used, with both a nuclear transformation vector encoding a GFP gene (pMON30098; FIG. 10) and a plastid transformation vector encoding both aadA and GFP genes (pMON49296; FIG. 4). The GFP gene on the pMON30098 vector is driven by the e35S promoter and has the hsp70 intron and therefore can only be expressed in the nucleus. This vector was included to monitor "transient" GFP expression useful to isolate those callus pieces that were productively hit during the transformation bombardment. After bombardment, selection for plastid transformants on streptomycin medium is achieved via the pMON49296 plastid-encoded aadA gene.

For bombardments, the standard DNA precipitation protocol was used, except that twice the amount of pMON30098 (2 μg/μL) was used relative to the pMON49296 (1 μg/μL) vector. Gold particles of 0.4 μm were used, a rupture disc pressure of 1350 psi, plate level 3 and 2 shots per plate. Tissues were placed on MS3 plus osmoticum prior to bombardment. After a one-day delay, bombarded tissues were transferred to MS3 plus streptomycin. A total of 24 plates of green multiple bud tissues were bombarded.

After the one-day delay period, all callus tissue was transferred to MS3 plus 100 μM streptomycin for selection. At ~4-week intervals, the callus tissue was subcultured to fresh MS3 medium plus streptomycin. Prior to the first subculture, the callus was observed under the fluorescence microscope for GFP activity. Callus pieces were divided into two types: good GFP expressors (treatment #1) and poor or no GFP expressors (treatment #2). It should be noted that GFP expression in this case was expected to be from the nuclear-encoded GFP gene, as transient expression from the plastid-encoded GFP gene is not expected to be visible at this early timepoint.

Callus from treatment #1 was first subcultured to 200, 500 or 1000 μM streptomycin. At the second subculture ~4 weeks later, all calli were subcultured to 1000 μM streptomycin. For treatment #2, at the second subculture, all callus was subcultured directly to 1000 μM streptomycin and maintained at that concentration throughout subsequent subcultures.

After ~5 months in culture, essentially all of the callus had turned yellow and appeared to be nonregenerable or was brown and dying. However, small GFP positive sectors of ~2 mm to ~4 mm were observed on 17 independent callus pieces. GFP fluorescence was observed in 11 callus pieces from treatment #1 and 6 callus pieces from treatment #2.

GFP fluorescence could arise from nuclear transformation of the pMON30098 construct and expression of its encoded GFP gene, from the plastid GFP gene on pMON49296 but from a nuclear insertion and fortuitous expression from a nuclear promoter, or from the plastid GFP gene after predicted insertion into the plastid genome and plastid expression. To prove plastid-localized expression of GFP in the callus lines, confocal microscopy was performed on several lines as shown in Table 3. Of 9 samples tested, confocal sample #6 (callus number 110-9) had exclusively a plastid localization of green GFP fluorescence. In addition to the predominantly green GFP fluorescence of plastids in sample 6, a few plastids showing only red chlorophyll autofluorescence were observed. These results indicate that callus 110-9 is a plastid transformant but still contains some wild-type plastids and is therefore heteroplasmic. Confocal microscopy sample #7 (callus number 110-5) showed some plastid-localized GFP expression, but also carried GFP localized to cell walls. This may indicate that this sample was transformed in both the plastid and the nucleus, but no further analysis of this sample was attempted.

TABLE 3

| Calli Number | Treatment # | GFP +/− | confocal sample # | GFP localization |
|---|---|---|---|---|
| 110-1aa | 1 | + | 3 | cell wall |
| 110-2 | 1 | + | 1 | cell wall |
| 110-3 | 1 | + | 4 | cell wall |
| 110-5 | 1 | + | 7 | cell wall/plastid |
| 110-8 | 1 | + | 5 | cell wall |
| 110-9 | 1 | + | 6 | Plastid |
| 110-13b | 2 | + | 8 | cell wall |
| 110-16b | 2 | + | 9 | cell wall |
| 110-17 | 2 | + | 2 | cell wall |

To confirm plastid transformation in callus 110-9 by molecular means, PCR analysis was performed. First, PCR primers were designed that distinguished between the nuclear GFP gene on plasmid pMON30098 (PCR pair GFP5":1/GFP3":2) (SEQ ID NO:28 and SEQ ID NO:29) and the plastid GFP gene on plasmid pMON49296 (PCR pair 202/201) (SEQ ID NO:30 and SEQ ID NO:31). Amplification of the 536 bp plastid GFP gene fragment was successful, whereas the nuclear GFP gene fragment did not amplify in callus 110-9. This result indicates that the plastid-localized GFP arises from expression of the gene from pMON49296, and therefore verifies plastid transformation in this sample. Additional PCR confirmation of plastid transformation in callus line 110-9 was obtained using primer pairs 198/199 (SEQ ID NO:32 and SEQ ID NO:33), 200/194 (SEQ ID NO:34 and SEQ ID NO:35) and 202/194 (SEQ ID NO:30 and SEQ ID NO:35) to successfully amplify the 492 bp aadA coding region fragment, the 545 bp fragment overlapping the GFP and aadA genes, and the 1065 bp larger fragment overlapping the GFP and aadA genes, respectively. Taken together, these results show that both the GFP and aadA transgenes reside in the plastid genome of the 110-9 line (FIG. 14).

Selection of Plastid Transformants in Green Multiple Bud Cultures Using CP4 as a Selectable Marker Plastid transformation vectors pMON56110 (FIG. 6) or pMON56114 (FIG. 8) (containing CP4 and GFP genes), pMON53161 (containing CP4 gene only) and pMON56101 (containing CP4 and aadA genes) were used for transformation of PHA green multiple bud cultures and glyphosate selection. Actively growing green callus pieces that are one to two weeks post subculture on fresh MS2 or MS3 medium were used as target material. Prior to bombardment, the leaves and leaf primordia were carefully removed. Callus pieces were arranged in the center of a plate (about 1.5 inches in diameter) containing MS2 or MS3 medium with or without osmoticum (0.2 M mannitol). In the case where osmoticum was used, the culture was incubated on osmoticum for 3-4 hr prior to bombardment. Post bombardment, the materials were removed from osmoticum to MS3 or MS2 medium the next day if osmoticum was used, or they were left on the same medium. After a delay time of 1-5 days, they were transferred to the same medium containing 10-25 µM of glyphosate for 2 weeks. They were then moved to 100-250 µM of glyphosate for the remaining selection period. The cultures were transferred to fresh selection medium at 3-4 week intervals. After 3-4 rounds of selection at the higher levels of glyphosate, most of the tissues turned yellow to brownish and eventually died. The tolerant, green pieces were moved to hormone-free medium without glyphosate for regeneration. It is also possible to use a steady-state concentration (100 µM) of glyphosate throughout the selection period, which is enough to inhibit growth of cells in culture but only gradually becomes lethal.

Samples of the tolerant lines are analyzed by PCR or Southern blotting at callus or plant stage to confirm the nature of tolerance.

Recovery of Plants from Putatively Transformed Sectors

Putatively transformed sectors are normally kept on selection to allow them to continue growth so that they can be regenerated. Under such circumstances, a couple of approaches will be taken to rescue the putative sectors. First, because the gfp gene is included in most of the vectors, GFP can be used as a "screenable" marker. The GFP positive sectors can be isolated under a dissecting microscope and placed on medium without any selective agent to allow the sectors to recover and to continue to grow by monitoring GFP expression; or the dissected sectors can be placed on media alternating with and without the selection to allow continued growth of the sectors without running the risk of losing the transformed copies of the plastid genomes; or the dissected sectors could be put on medium with low levels of selection to balance the growth and maintenance of the transformed copies. Second, the dissected sectors could also be placed on top of nurse cultures, which are resistant to glyphosate, in the presence of glyphosate for a period of time to help the putative sectors to grow and to amplify its transgenic copies of the plastid genome.

Example 3

Greening Embryogenic Callus as Target Material

Light-grown multiple bud cultures have been shown above to be successful for plastid transformation. However, the frequency of transformation in the light-grown cultures is very low. In contrast, dark-grown embryogenic callus is typically highly transformable when nuclear transformation is performed, but these cultures contain only undeveloped plastids and so may not be ideal for plastid transformation. "Greening" embryogenic cultures that contain more developed plastids but still maintain the high transformability of dark-grown cultures would be advantageous and may be useful as target materials for plastid transformation.

To establish greening embryogenic cultures, dark-grown embryogenic callus must first be initiated. Young ears of inbred or hybrid maize lines (e.g., H99, PHA for Type I embryogenic callus and HiII or LH198×HiII for Type II embryogenic callus) are sterilized in 50% bleach (bleach contains 5.25% sodium hypochlorite) for 20 min and washed with sterile water 3 times. Immature embryos are isolated and cultured with scutellum side facing up on callus induction media, which differs depending on the plant genotype as shown in Table 1. The embryo cultures are kept in the dark culture room at 26-27° C. Embryogenic callus that develops from the embryos is maintained on the same medium through routine subculture every 2 to 3 weeks.

For greening embryogenic cultures, the dark-grown embryogenic calli are spread out on MS2 or MS3 media and cultured at 26° C. with 16 hr light/8 hr darkness. The somatic embryos start to green up from the embryo side within 3-10 days. The greening somatic embryos are then picked up and used as the target material for bombardment using the helium gun. In some cases, it may be desirable to bombard the dark-grown embryogenic callus prior to incubation in the light and subsequently perform the selection on MS2 or MS3 greening medium in the light.

For streptomycin selection experiments, tissues are maintained on the same medium for a one-day delay period before selection. The tissues are then placed on MS2 or MS3 selection media with 50 or 100 mg/L streptomycin. This selection level allows for shoot development and callus growth at a slightly inhibited level but also allows bleaching of nontransformed tissue. At approximately monthly intervals, the growing tissue is separated from the dead and non-regenerable tissue and the leaves are peeled away from the callus. The callus pieces are then placed on higher concentrations of streptomycin at levels of 100 or 200 mg/L. This level decreases the regenerability of nontransformed cells, greatly reducing the growth of the callus. After further selection for one month, the living green tissue is placed on hormone-free regeneration media. Shoots that emerge as green or GFP positive are further analyzed. In some cases, it may be desirable to increase the streptomycin concentration to 500 or 1000 mg/L for one subculture prior to plant regeneration to further eliminate any possibility of non-transformed cells.

For glyphosate selection experiments, greening type II embryogenic calli (e.g., LH198×HiII or HiII) are selected on MS2 or MS3 media initially with 10-25 µM of glyphosate for about 2 weeks, then stepping up to 100-250 µM glyphosate. At 100-250 µM glyphosate, growth is dramatically inhibited and the non-transformed tissues eventually die.

Example 4

Dark-Grown Embryogenic Callus Cultures as Target Material

Dark-grown embryogenic callus cultures of various genotypes (e.g., LH198×HiII or HiII) were established from immature embryos as described previously and maintained in continuous dark at 26° C. Callus is subcultured at intervals of about every 2 weeks.

For bombardment of dark grown callus, embryogenic pieces of about 1-2 mm are placed on a filter paper on top of callus induction media. For glyphosate selection, the calli are incubated on osmoticum-containing medium for 3-4 hr prior to bombardment, followed by 1-4-day delay on maintenance medium without glyphosate post bombardment. They are then placed on the first selection of 100-500 µM glyphosate for one week. The selection level is subsequently increased to 500 µM then 1 mM, until it reaches 3 mM. After several rounds of subculture on 3 mM, distinct, glyphosate-tolerant callus will be obtained. They will then be placed on hormone-free medium for regeneration.

Example 5

Pre-Cultured Immature Embryos as Target Material Using Glyphosate Selection

Genotypes of LH198×HiII or HiII (derivative of A188× B73) were used as the source for immature embryos. Ten days after pollination, the ears were harvested and within 5 days of the harvest date the immature embryos were excised. The corn ears were sterilized with 50% bleach (v/v) with 2 drops of Tween-20 for 20 min. They were then rinsed three times with sterile distilled water. Using a scalpel, the tops of the kernels were removed. Using a small spatula, the embryo was excised and placed onto N6 media with $AgNO_3$ and 3% sucrose, with scutellum side away from media. The immature embryos were pre-cultured in the dark at 28° C. for 3 days.

Prior to bombardment, about 50 embryos were arranged into a 2 cm diameter circle onto the same N6 medium plus osmoticum. Bombardment used M5 tungsten particles and the standard DNA precipitation procedures. Ten µL of DNA/tungsten mix was added to each macrocarrier. Each plate was bombarded twice at sample level L3 (9 cm) and rupture pressure 1350 psi. Approximately two hours after bombardment, the embryos were removed from osmoticum media and placed back onto N6 medium for 5-6 days in the dark at 28° C. After this delay period, the coleoptiles of the embryos were removed and the embryos were transferred to N6 medium with 50 µM glyphosate. After two weeks the explants were transferred to N6 plus 500 µM glyphosate, and callus was spread with a spatula if needed. Every two weeks the tissue was transferred to fresh selection medium, and cultured at 28° C. in the dark.

Example 6

Nuclear Transformation Using aadA or CP4 Selection

Light-grown multiple bud culture of PHA was used for the nuclear transformation. The vectors pMON38762 and pMON45294 (see the section describing the vectors) were bombarded using similar parameters. For streptomycin selection, MS3 medium supplemented with 500 and 1000 mg/L of selective agent was used. GFP positive shoots were selected in both cases. Of a total of 224 pieces of the light-grown green multiple bud tissue bombarded with pMON38762 (cytoplasmic aadA), over 10 independently transformed callus lines were obtained by selection on medium containing a combination of streptomycin and spectinomycin each at 1000 mg/L. Transformation frequency was slightly lower with nuclear CTP:aadA construct pMON45294.

Light-grown multiple bud cultures of PHA were also used for glyphosate selection according to the same transformation protocol as and following similar selection regimes to plastid transformation. A CP4 vector and a gfp vector were co-bombarded into the green multiple bud tissue. The former allows for selection of the transformed cells, whereas the later allows for identification and monitoring of the transformed sectors. Following a few rounds of selection at 100-250 µM of glyphosate, some green tolerant clones were identified. These clones will be analyzed molecularly to confirm the insertion of the transgenes into the nuclear genome.

For selection of the dark-grown embryogenic calli with glyphosate, LH198×HiII calli were placed on filter paper on osmoticum-containing medium and incubated for 4 hr before bombardment. They were bombarded with 0.6µ gold particles coated with equal amounts of pMON30098 (containing GFP) and pMON25496 (containing CP4) and bombarded at 1100 psi according to the Standard Operation Protocol for the Biolistic PDS-1000/He particle gun. After a delay of 4 days on the maintenance medium, the calli were selected on 1 mM glyphosate for 2 weeks, followed by 3 mM for several rounds, each for 2 weeks. At the end of $4^{th}$ round of 3 mM glyphosate, glyphosate-tolerance and GFP expression were recorded. Forty-six percent of the initially bombarded calli were tolerant to glyphosate. Among the glyphosate-tolerant clones, over 40% also showed various levels of GFP expression, ranging from spotty to uniform, from very weak to very strong GFP expression.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention which is defined by the following claims.

The invention claimed is:

1. A method for transforming a plastid of a maize cell, said method comprising:
   (a) culturing an immature embryo of a maize plant in the presence of light to obtain a seedling;
   (b) culturing a nodal section from said seedling in a medium comprising cytokinin in the presence of light to obtain a green multiple bud culture;
   (c) introducing an exogenous DNA molecule of interest comprising an expression cassette into at least one cell of said green multiple bud culture, wherein said expression cassette is expressible in a plastid and becomes integrated into a plastid genome of said at least one cell; and
   (d) selecting for at least one plastid transformed maize cell from said green multiple bud culture comprising said expression cassette.

2. The method of claim 1, wherein said nodal section comprises meristematic tissue.

3. The method of claim 1, wherein said medium further comprises an auxin.

4. The method of claim 1, wherein said cytokinin is benzyl adenine (BA) or picloram.

5. The method of claim 1, wherein said exogenous DNA molecule is introduced into at least one cell of said green multiple bud culture through particle bombardment.

6. The method of claim 1, wherein said expression cassette comprises a selectable marker gene conferring tolerance to a selective agent, and wherein said selecting step comprises selection with said selective agent.

7. The method of claim 6, wherein said selectable marker gene is an aadA gene and said selective agent is spectinomycin or streptomycin.

8. The method of claim 6, wherein said selectable marker gene is a CP4 gene and said selective agent is glyphosate.

9. The method of claim 6, wherein said selectable marker gene is under the control of a plastid functional promoter.

10. The method of claim 6, wherein said expression cassette further comprises a screenable marker gene.

11. The method of claim 10, wherein said screenable marker gene is a GFP gene.

12. The method of claim 1, wherein said maize plant is selected from the group consisting of H99, (PA91×H99)× A188, Honey and Pearl, HiII and LH198×HiII.

13. The method of claim 1, wherein said expression cassette is integrated into the rbcL-psaI intergenic region of the Large Single Copy region of the maize plastid genome or the rrn16/trnV-rps12/3'-rps7 intergenic region of the Inverted Repeat region of the maize plastid genome.

14. A method of producing a transplastomic maize plant, said method comprising:
   (a) transforming a plastid of at least one maize plant cell according to the method of claim 1; and
   (b) regenerating a maize plant from the at least one plastid transformed maize plant cell to produce said transplastomic maize plant.

* * * * *